(12) United States Patent
Lee et al.

(10) Patent No.: US 8,191,550 B2
(45) Date of Patent: *Jun. 5, 2012

(54) METHOD AND APPARATUS TO RELIEVE MENSTRUAL PAIN

(75) Inventors: Stephen D. Lee, Sarasota, FL (US); Glenn Akhavein, Bradenton, FL (US); Robert Brady, Sarasota, FL (US); Daniel Dugas, Sarasota, FL (US)

(73) Assignee: Embrace, LLC, Sarasota, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/824,789

(22) Filed: Jun. 28, 2010

(65) Prior Publication Data

US 2011/0015708 A1 Jan. 20, 2011

Related U.S. Application Data

(63) Continuation-in-part of application No. 12/404,655, filed on Mar. 16, 2009, and a continuation-in-part of application No. 11/753,562, filed on May 24, 2007, now abandoned.

(51) Int. Cl.
*A61F 5/28* (2006.01)
*A61F 5/30* (2006.01)
*A61F 5/24* (2006.01)

(52) U.S. Cl. ............... 128/99.1; 128/102.1; 128/106.1; 128/115.1; 128/121.1

(58) Field of Classification Search .............. 128/96.1, 128/95.1, 98.1, 99.1, 100.1, 102.1, 104.1, 128/106.1, 107.1, 115.1, 845, 846, 869, 882; 602/19, 53; 606/201, 203, 55; 474/153, 474/163

See application file for complete search history.

(56) References Cited

U.S. PATENT DOCUMENTS

| 35,038 | A |   | 4/1862  | Pierce       |        |
|--------|---|---|---------|--------------|--------|
| 1,600,178 | A |   | 9/1926  | Hussey    |        |
| 1,660,451 | A | * | 2/1928  | Linney .............................. 2/322 |
| D99,529 | S |   | 5/1936  | Spanel      |        |
| 2,018,981 | A |   | 10/1938 | Tietjen    |        |
| D134,791 | S |   | 1/1943  | Selver      |        |
| 2,453,370 | A |   | 11/1948 | Hittenberger |      |
| 2,493,406 | A |   | 1/1950  | Hicks, III  |        |
| 2,497,443 | A | * | 2/1950  | Eatman ......................... 607/108 |

(Continued)

FOREIGN PATENT DOCUMENTS

JP 2007075304 3/2007

(Continued)

*Primary Examiner* — Patricia Bianco
*Assistant Examiner* — Ophelia Hawthorne
(74) *Attorney, Agent, or Firm* — Allen, Dyer, Doppelt, Milbrath & Gilchrist, P.A.

(57) ABSTRACT

An apparatus to relieve menstrual cramping includes one or more tapered pads having an inner and outer side, each outer side being semi-rigid and each inner side being flexible. The outer side of each pad is connected to one or more straps having first and second ends. A fastener is attached to the first end of each strap and a corresponding second fastener attaches to the second end of each strap. The apparatus includes a variable compression drive located proximate to one pad to create a compression force through each strap when the first and corresponding second fasteners connect. The drive includes an outer drum shell, an inner rotator having an inner diameter that is treaded, a motor which communications with the inner rotator, and a threaded shaft which engages the inner diameter of the inner rotator. A tab attaches the threaded shaft to the strap.

19 Claims, 32 Drawing Sheets

U.S. PATENT DOCUMENTS

| | | | |
|---|---|---|---|
| 2,552,475 | A | 5/1951 | Austlid |
| 2,590,212 | A | 3/1952 | Samuels |
| 2,652,051 | A | 9/1953 | Hoover |
| 2,654,366 | A | 10/1953 | Miller |
| 2,813,526 | A | 11/1957 | Beebe |
| 2,828,737 | A | 4/1958 | Hale |
| 3,071,133 | A | 1/1963 | Eisen |
| 3,351,053 | A | 11/1967 | Stuttle |
| 3,393,674 | A | 7/1968 | Nelkin |
| 3,396,264 | A | 8/1968 | Murphy et al. |
| 3,500,014 | A | 3/1970 | Longo |
| 3,501,616 | A | 3/1970 | Arron |
| 3,518,995 | A | 7/1970 | Claff |
| 3,548,817 | A | 12/1970 | Mittasch |
| 3,577,986 | A | 5/1971 | Regent et al. |
| 3,680,563 | A | 8/1972 | Forrest |
| 3,797,501 | A | 3/1974 | DiTullio |
| 4,122,552 | A | 10/1978 | Tedford |
| D258,770 | S | 4/1981 | Stern |
| 4,577,622 | A | 3/1986 | Jennings |
| 4,580,555 | A | 4/1986 | Coppess |
| 4,622,957 | A | 11/1986 | Curlee |
| 4,671,264 | A | 6/1987 | Frangi |
| 4,675,918 | A | 6/1987 | O'Brien |
| 4,681,113 | A | 7/1987 | Coplans |
| 4,715,364 | A | 12/1987 | Noguchi |
| 4,912,813 | A | 4/1990 | Muller et al. |
| 4,937,887 | A | 7/1990 | Schreiner |
| 4,957,105 | A | 9/1990 | Kurth |
| 4,993,409 | A | 2/1991 | Grim |
| 5,129,647 | A | 7/1992 | Castellanos |
| 5,363,863 | A | 11/1994 | Lelli et al. |
| 5,383,893 | A | 1/1995 | Daneshvar |
| 5,383,920 | A | 1/1995 | Sikes |
| 5,388,274 | A | 2/1995 | Glover et al. |
| 5,407,422 | A | 4/1995 | Matthijs et al. |
| 5,437,618 | A | 8/1995 | Sikes |
| 5,476,492 | A | 12/1995 | Unrug |
| 5,486,680 | A | 1/1996 | Lieberman |
| 5,528,775 | A | 6/1996 | Marenda |
| 5,551,093 | A | 9/1996 | Stricker |
| 5,588,186 | A | 12/1996 | Ko |
| 5,628,721 | A | 5/1997 | Arnold et al. |
| D380,051 | S | 6/1997 | Davis et al. |
| 5,647,824 | A | 7/1997 | Levenson |
| 5,690,122 | A | 11/1997 | Weber-Unger |
| 5,701,608 | A | 12/1997 | Kohn |
| 5,728,055 | A | 3/1998 | Sebastian |
| 5,782,781 | A | 7/1998 | Nagaoka |
| 5,799,650 | A | 9/1998 | Harris |
| 5,817,145 | A | 10/1998 | Augustine et al. |
| 5,830,168 | A | 11/1998 | Finnell et al. |
| 5,893,368 | A | 4/1999 | Sugerman |
| 5,913,410 | A | 6/1999 | Tsuchiya |
| 5,947,914 | A | 9/1999 | Augustine |
| 5,954,680 | A | 9/1999 | Augustine |
| 5,964,721 | A | 10/1999 | Augustine |
| 5,964,723 | A | 10/1999 | Augustine |
| 5,986,163 | A | 11/1999 | Augustine |
| 6,010,527 | A | 1/2000 | Augustine et al. |
| 6,013,097 | A | 1/2000 | Augustine et al. |
| 6,045,518 | A | 4/2000 | Augustine |
| 6,065,166 | A | 5/2000 | Sharrock et al. |
| 6,066,109 | A | 5/2000 | Buser et al. |
| 6,071,254 | A | 6/2000 | Augustine |
| 6,093,160 | A | 7/2000 | Augustine et al. |
| 6,099,490 | A | 8/2000 | Turtzo |
| 6,110,197 | A | 8/2000 | Augustine et al. |
| 6,213,966 | B1 | 4/2001 | Augustine |
| 6,217,535 | B1 | 4/2001 | Augustine |
| 6,235,049 | B1 | 5/2001 | Nazerian |
| 6,241,693 | B1 | 6/2001 | Lambden |
| 6,241,697 | B1 | 6/2001 | Augustine |
| 6,248,084 | B1 | 6/2001 | Augustine et al. |
| 6,264,622 | B1 | 7/2001 | Augustine |
| 6,267,740 | B1 | 7/2001 | Augustine et al. |
| 6,293,917 | B1 | 9/2001 | Augustine et al. |
| 6,328,627 | B1 | 12/2001 | Smith |
| 6,406,448 | B1 | 6/2002 | Augustine |
| 6,407,307 | B1 | 6/2002 | Augustine |
| 6,419,651 | B1 | 7/2002 | Augustine |
| 6,423,018 | B1 | 7/2002 | Augustine |
| 6,460,195 | B2 | 10/2002 | Wang |
| 6,465,708 | B1 | 10/2002 | Augustine |
| 6,468,295 | B2 | 10/2002 | Augustine et al. |
| 6,580,012 | B1 | 6/2003 | Augustine et al. |
| 6,592,428 | B2 | 7/2003 | Smith |
| 6,605,051 | B2 | 8/2003 | Augustine |
| 6,613,034 | B2 | 9/2003 | Nozaki et al. |
| 6,634,533 | B2 | 10/2003 | Thompson et al. |
| 6,820,574 | B2 | 11/2004 | Sharpe |
| 6,840,915 | B2 | 1/2005 | Augustine |
| 6,921,374 | B2 | 7/2005 | Augustine |
| 6,987,209 | B2 | 1/2006 | Augustine et al. |
| 7,008,389 | B2 | 3/2006 | Krieg et al. |
| 7,066,181 | B2 | 6/2006 | West |
| 7,122,046 | B2 | 10/2006 | Augustine et al. |
| 7,230,819 | B2 | 6/2007 | Muchow et al. |
| 2008/0068782 | A1 | 3/2008 | Muchow et al. |
| 2008/0289623 | A1 | 11/2008 | Lee |

FOREIGN PATENT DOCUMENTS

| | | | |
|---|---|---|---|
| KR | 20090049805 | | 5/2009 |

* cited by examiner

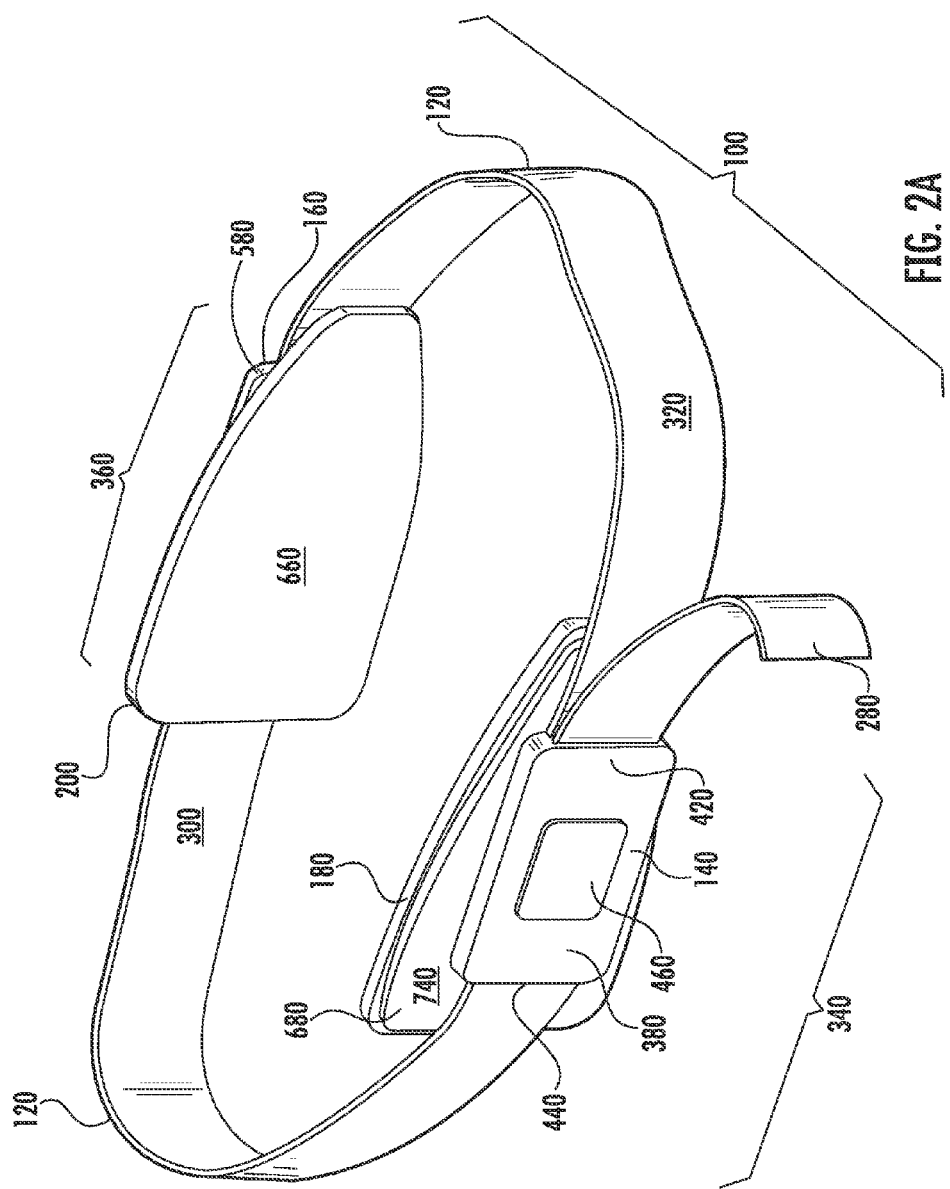

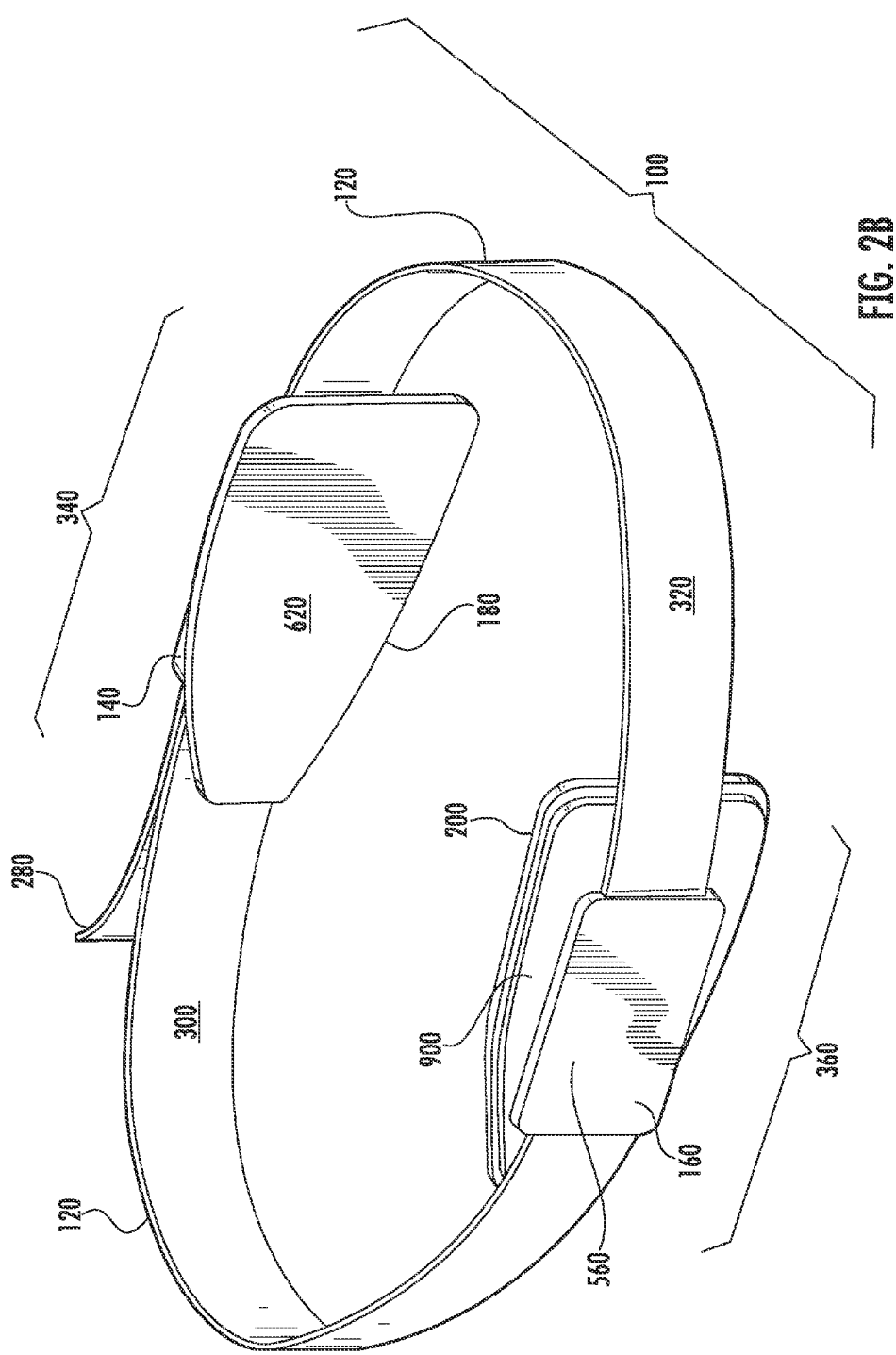

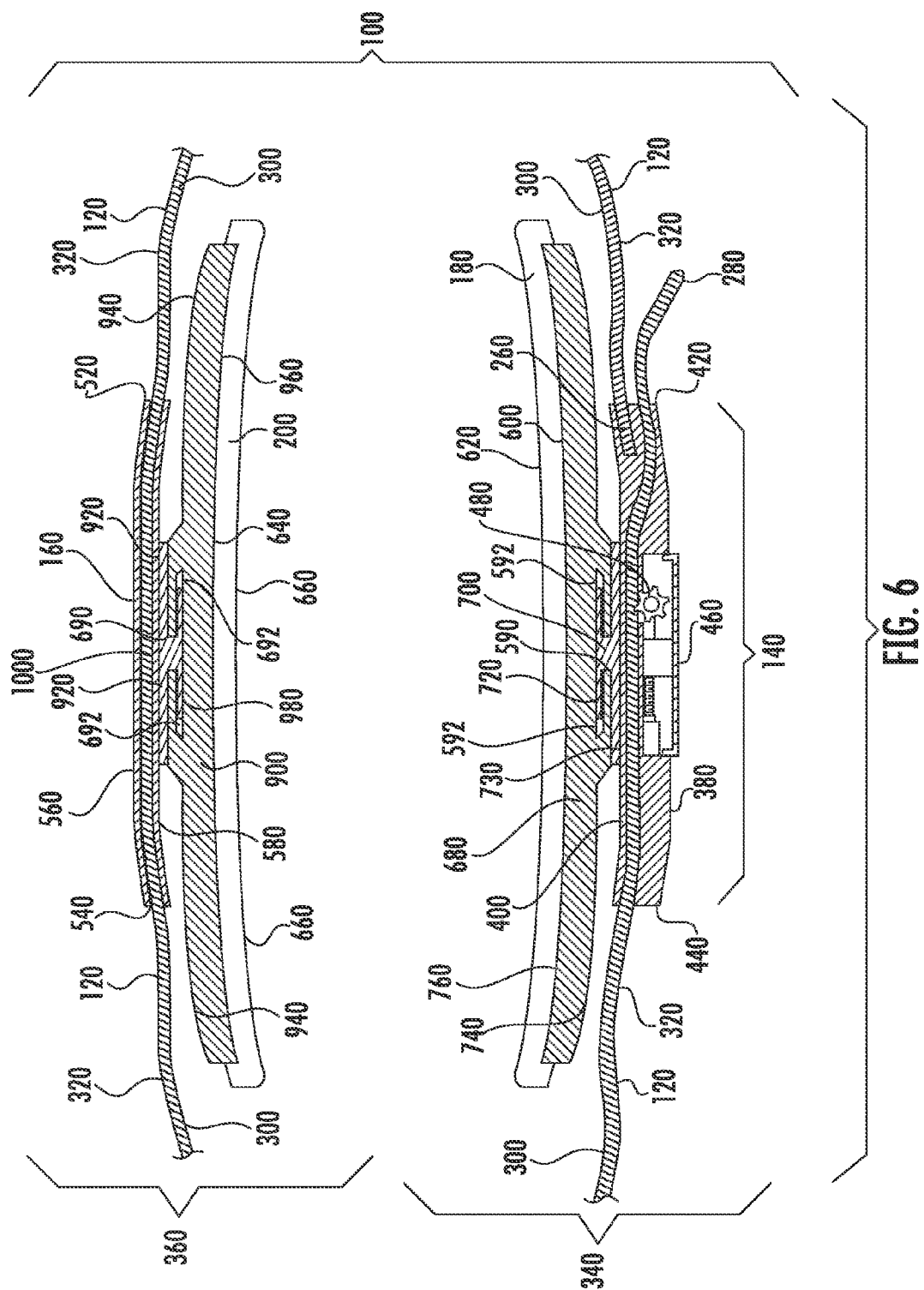

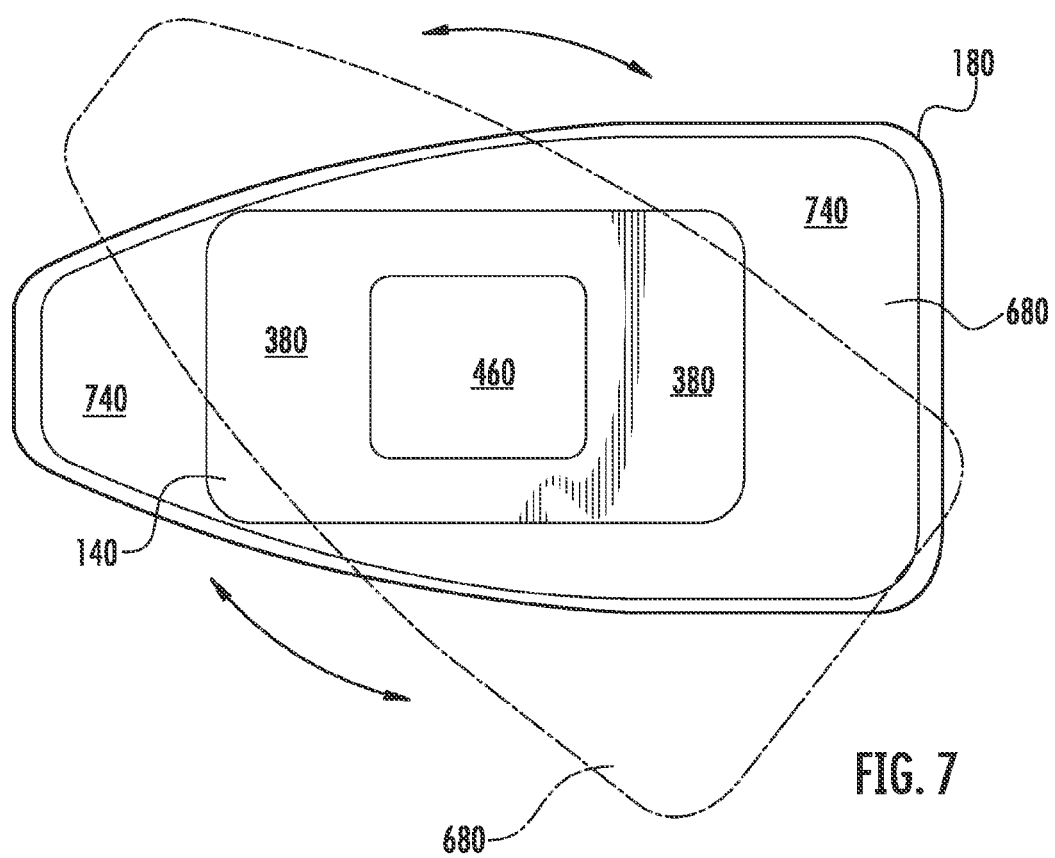

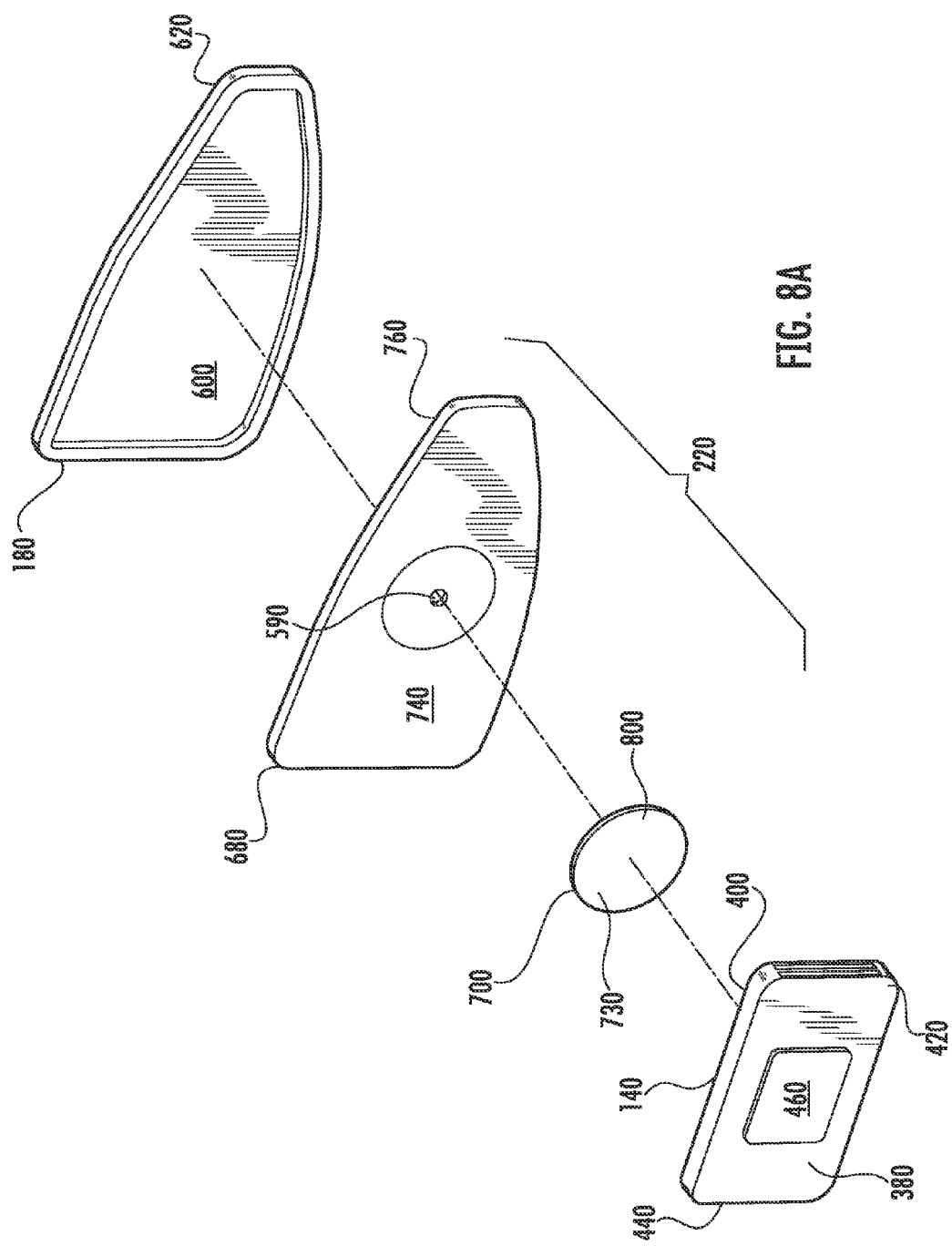

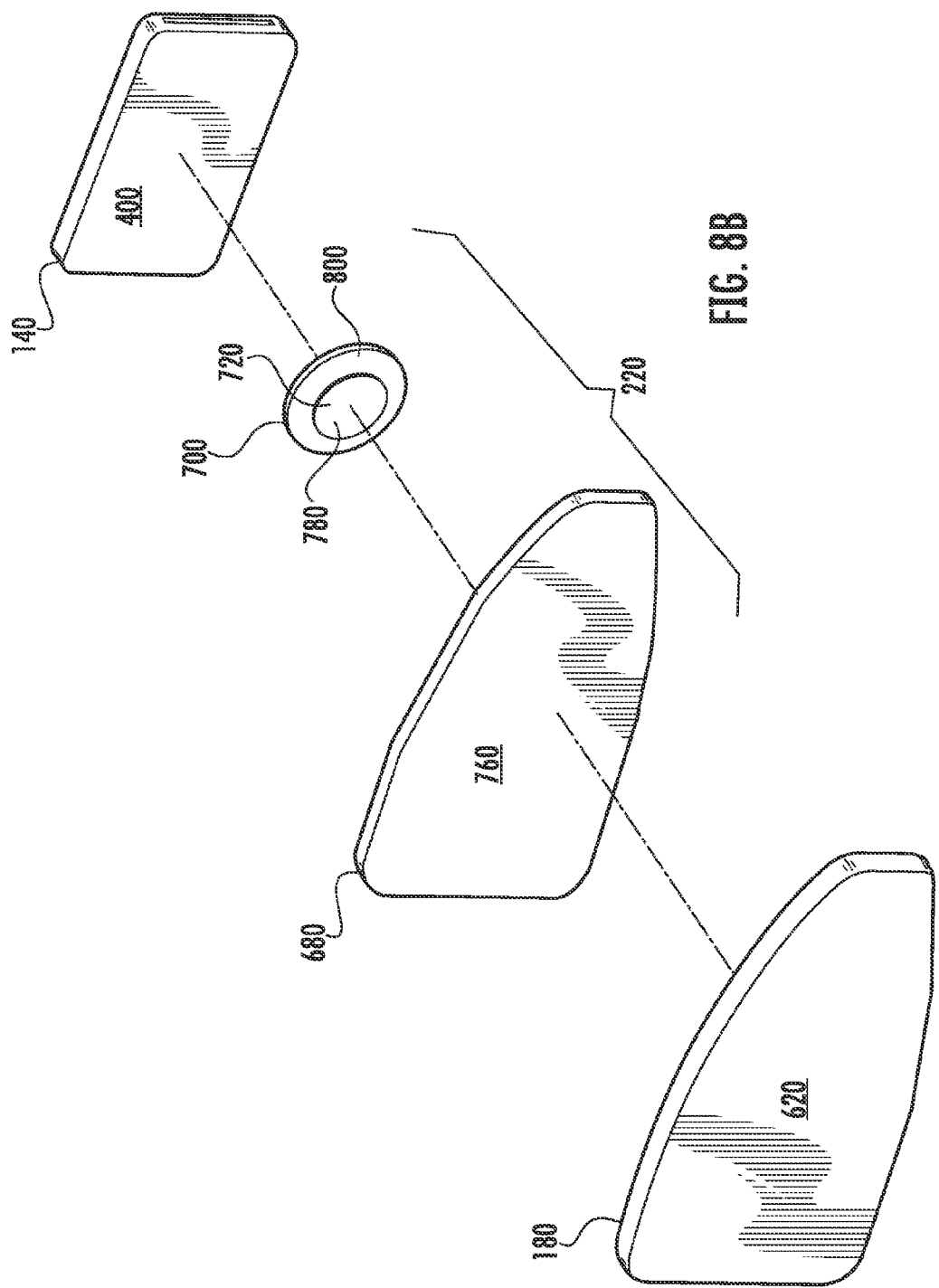

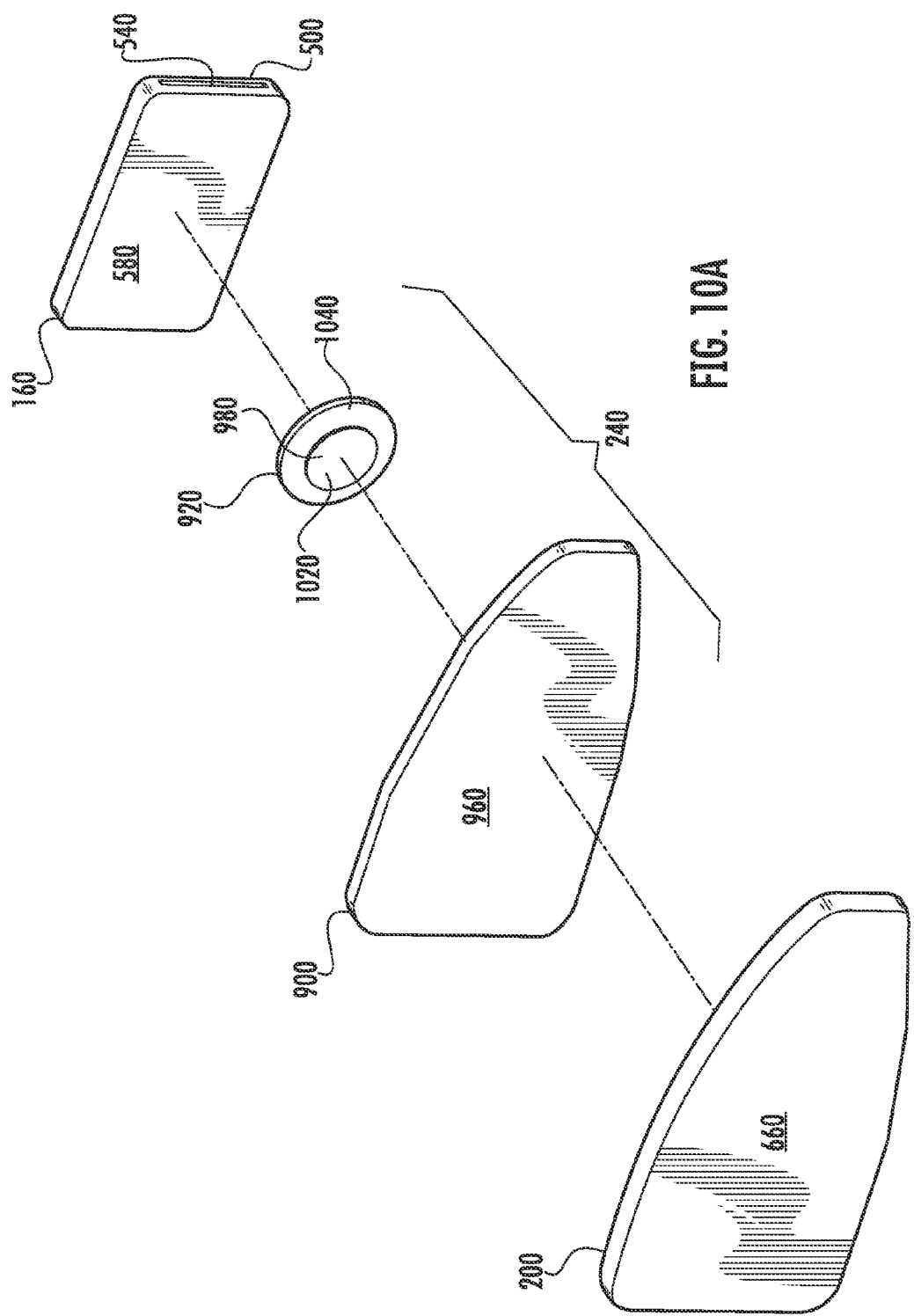

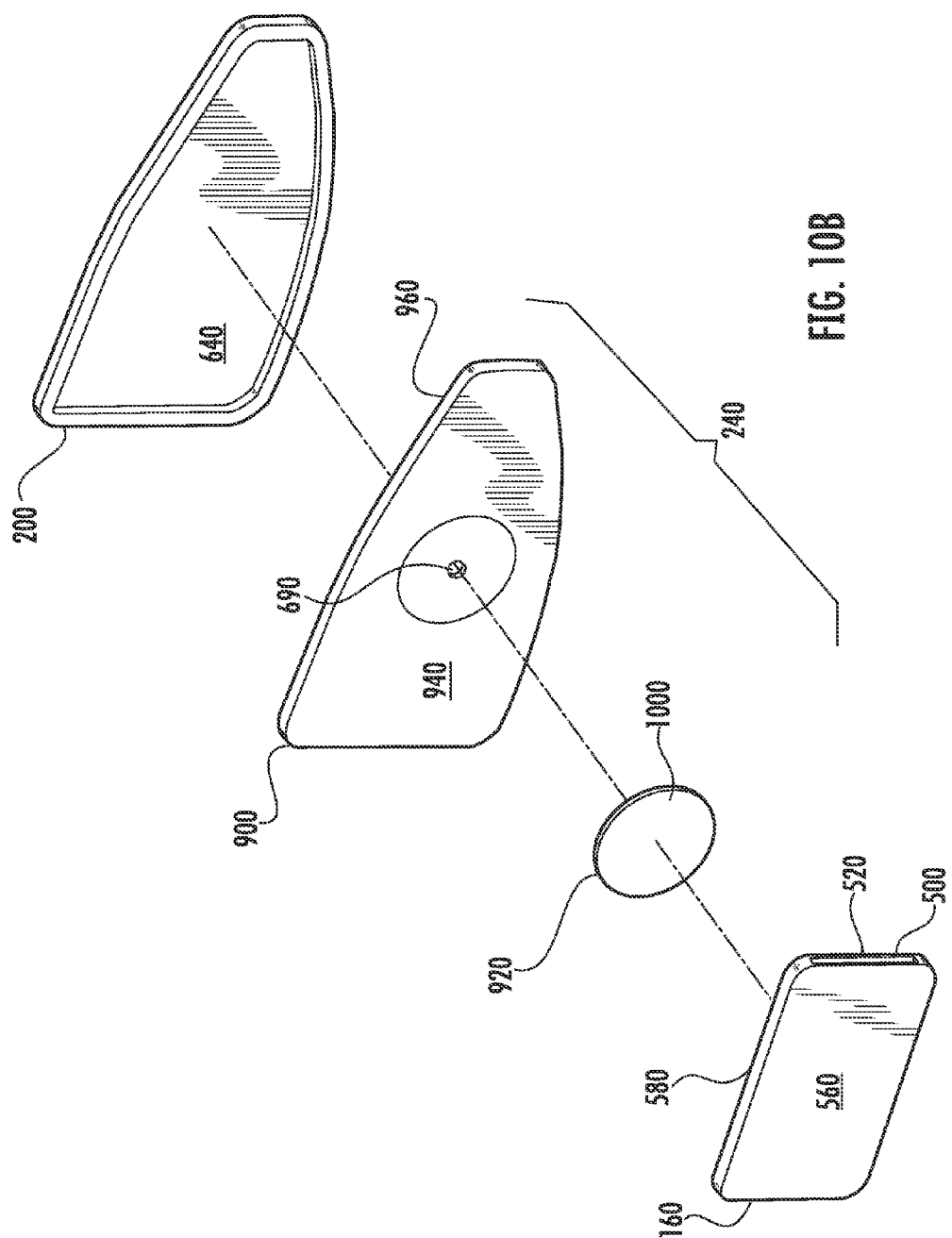

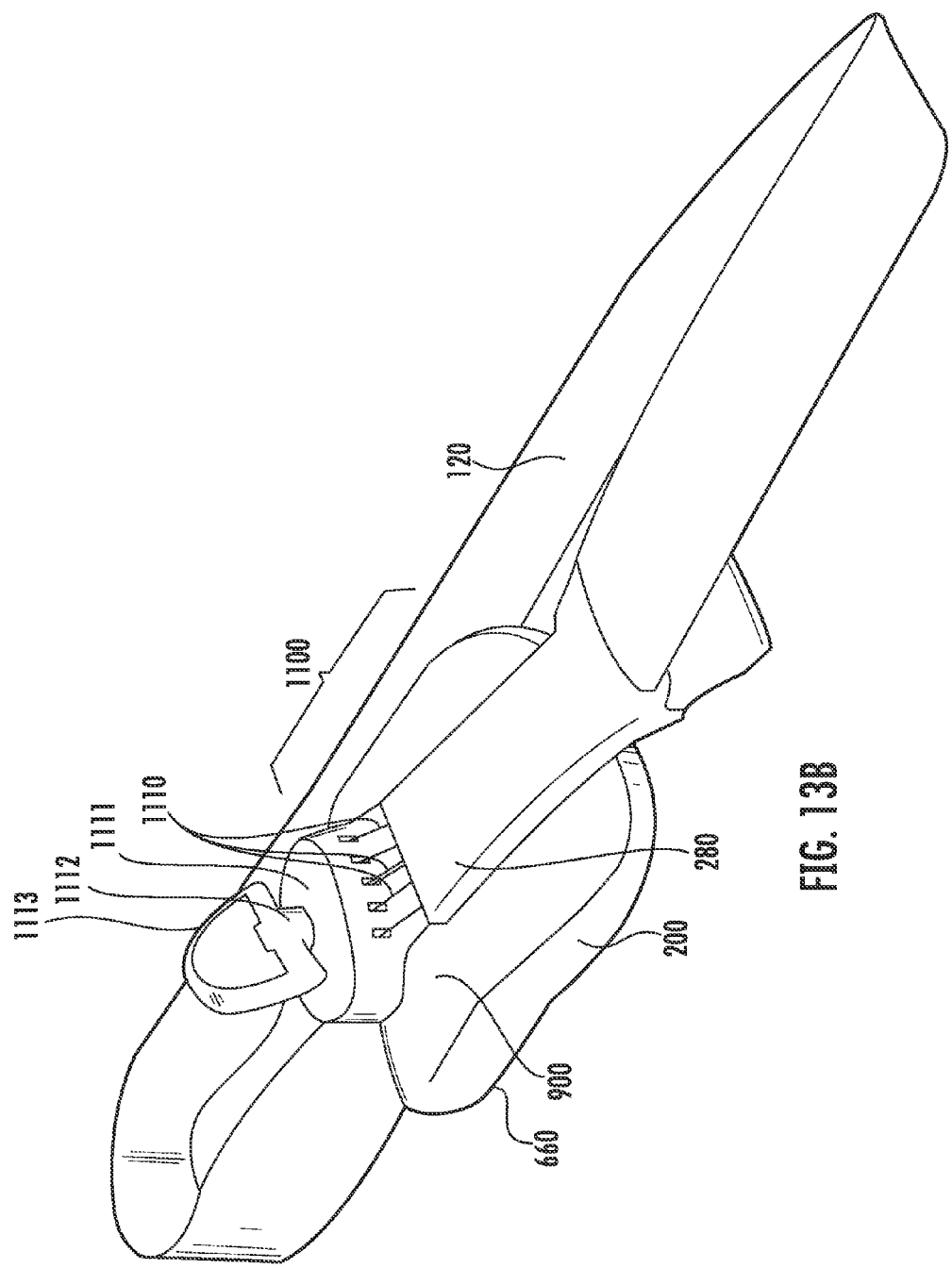

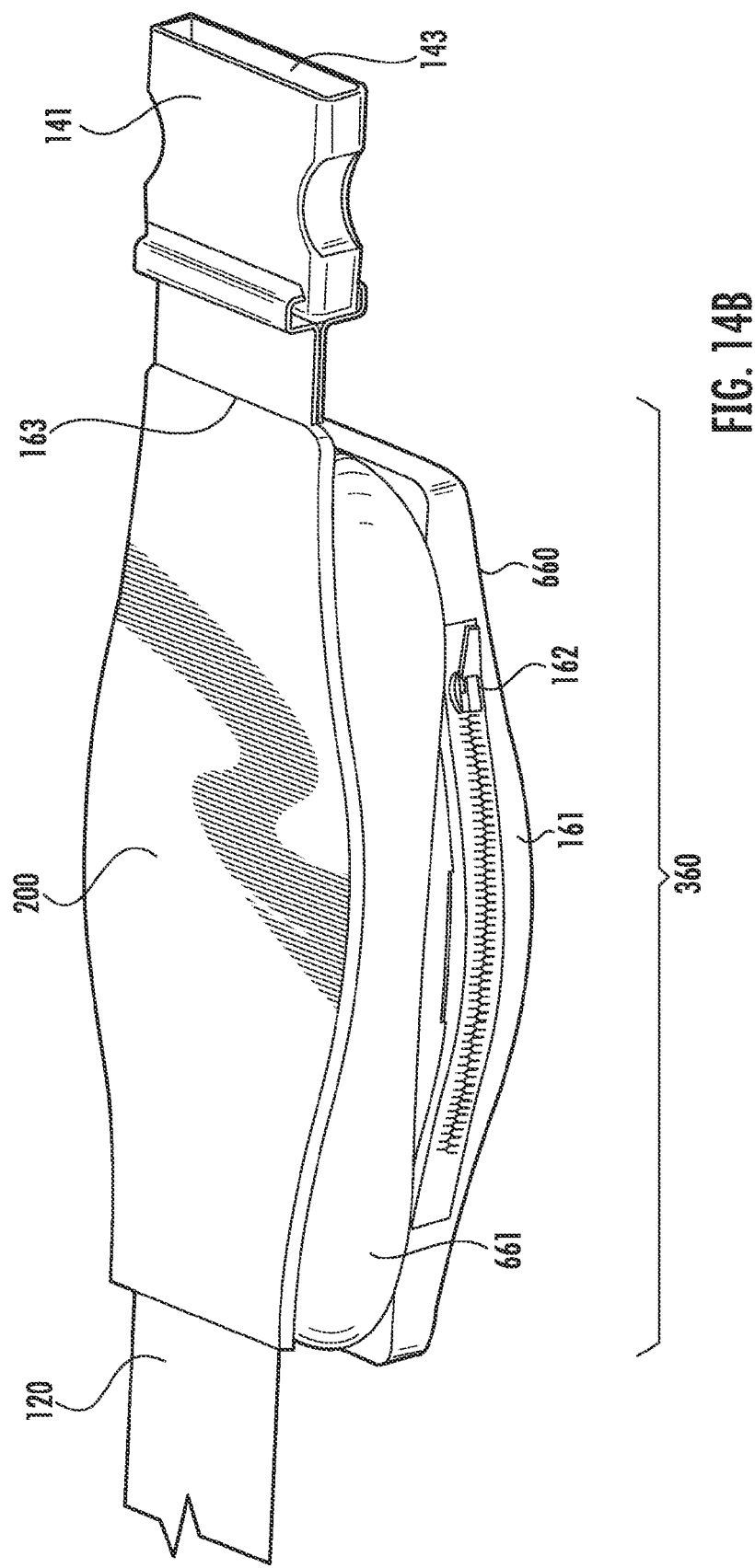

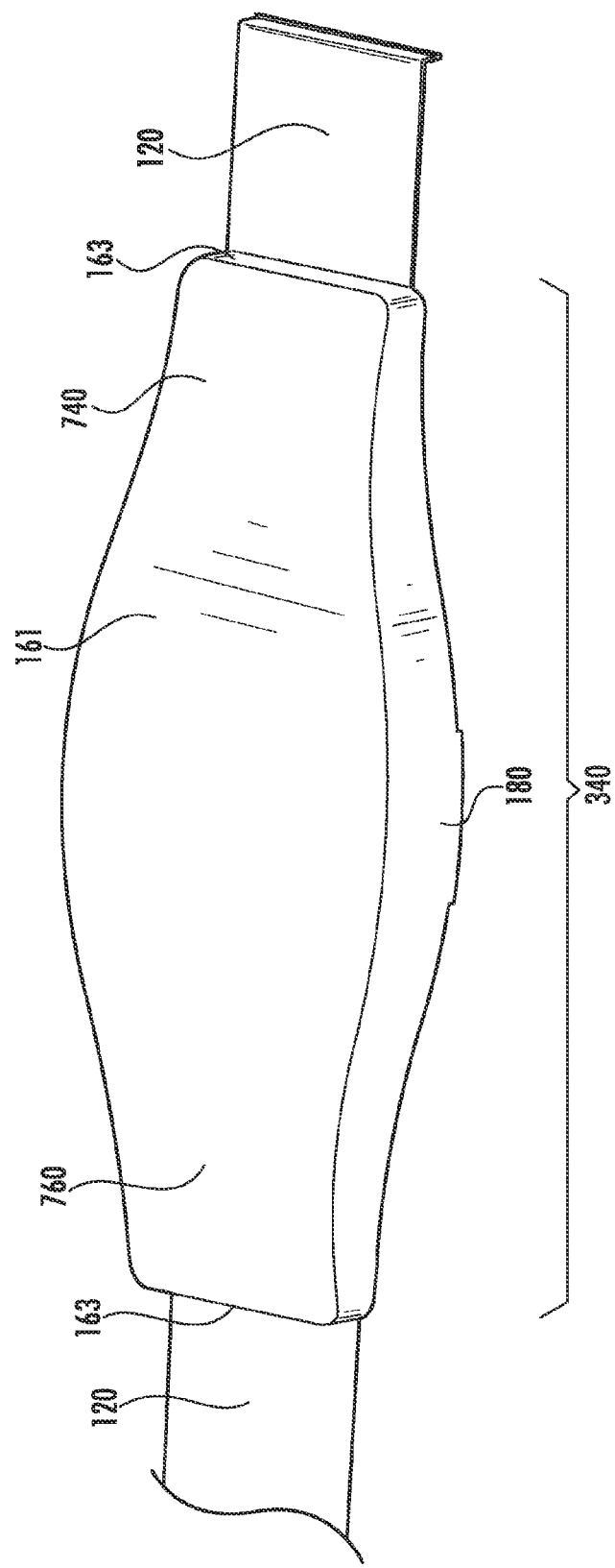

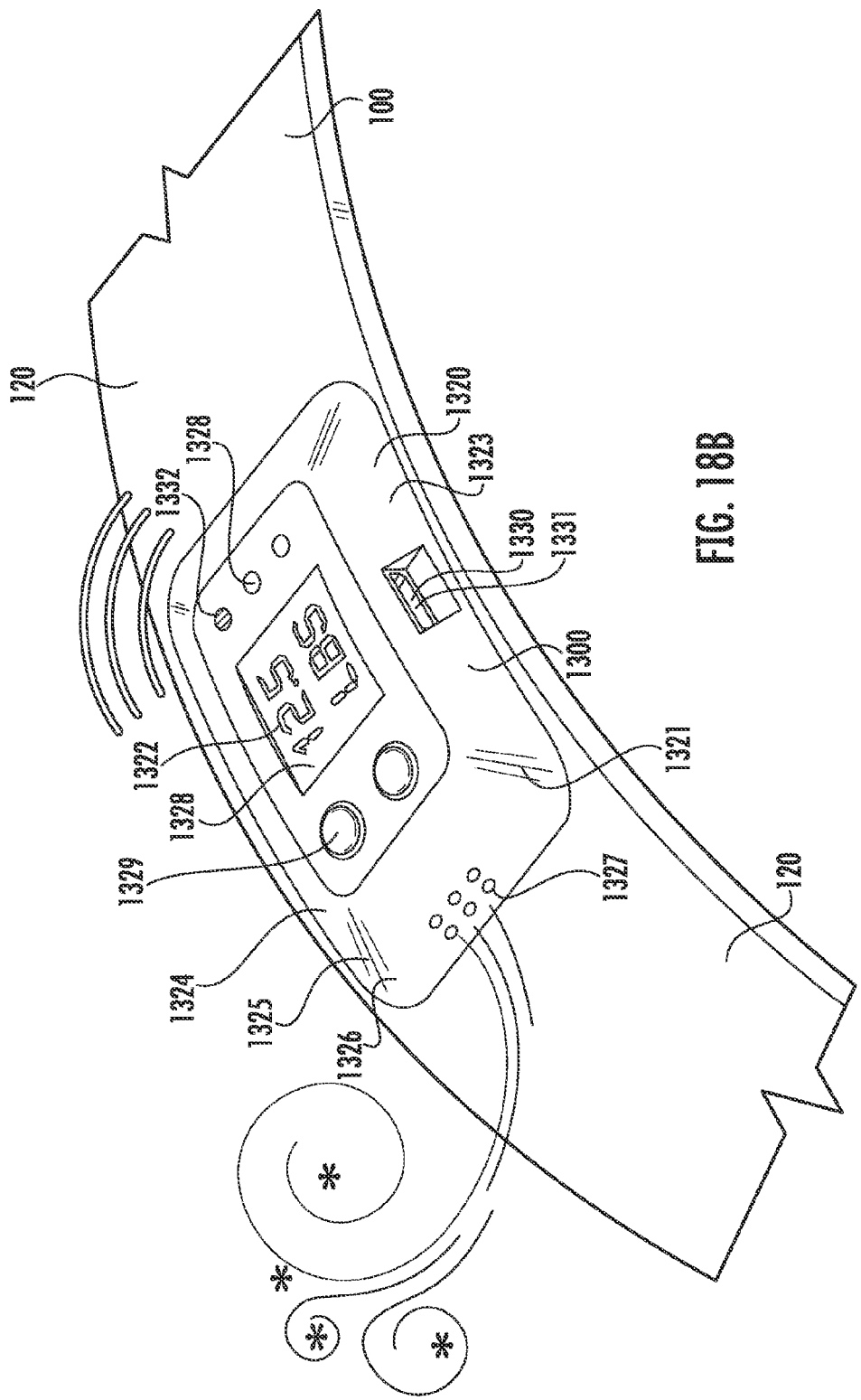

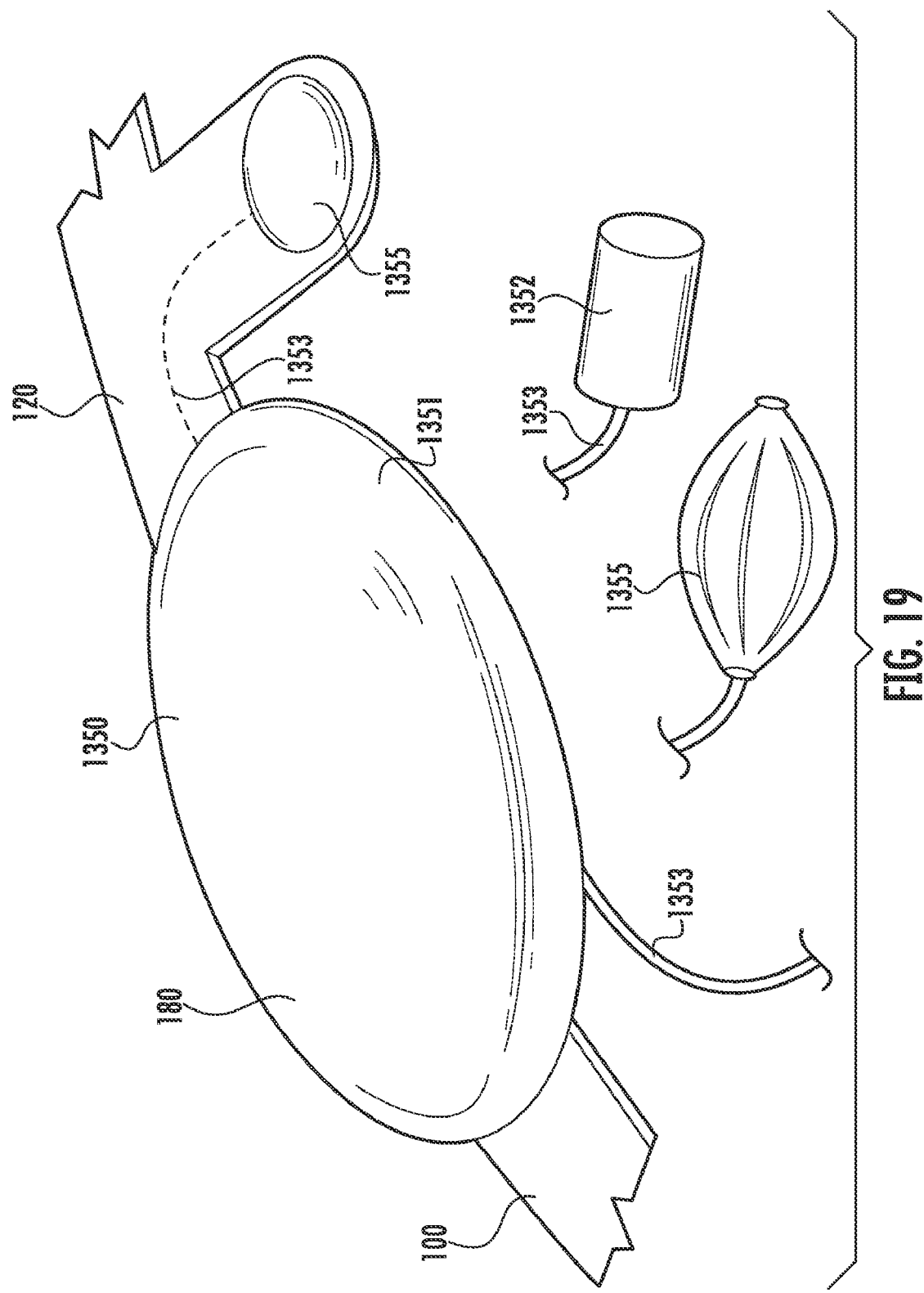

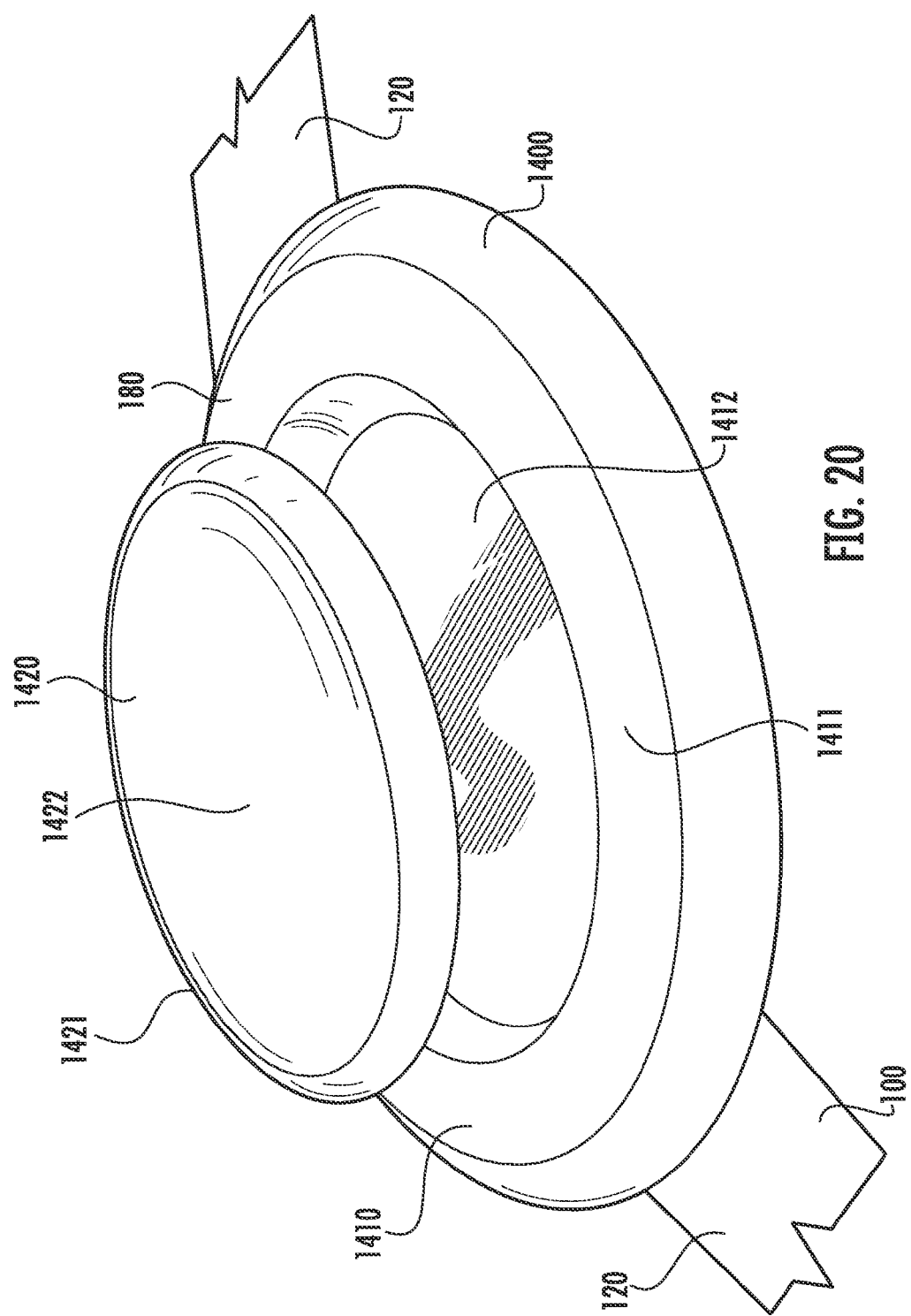

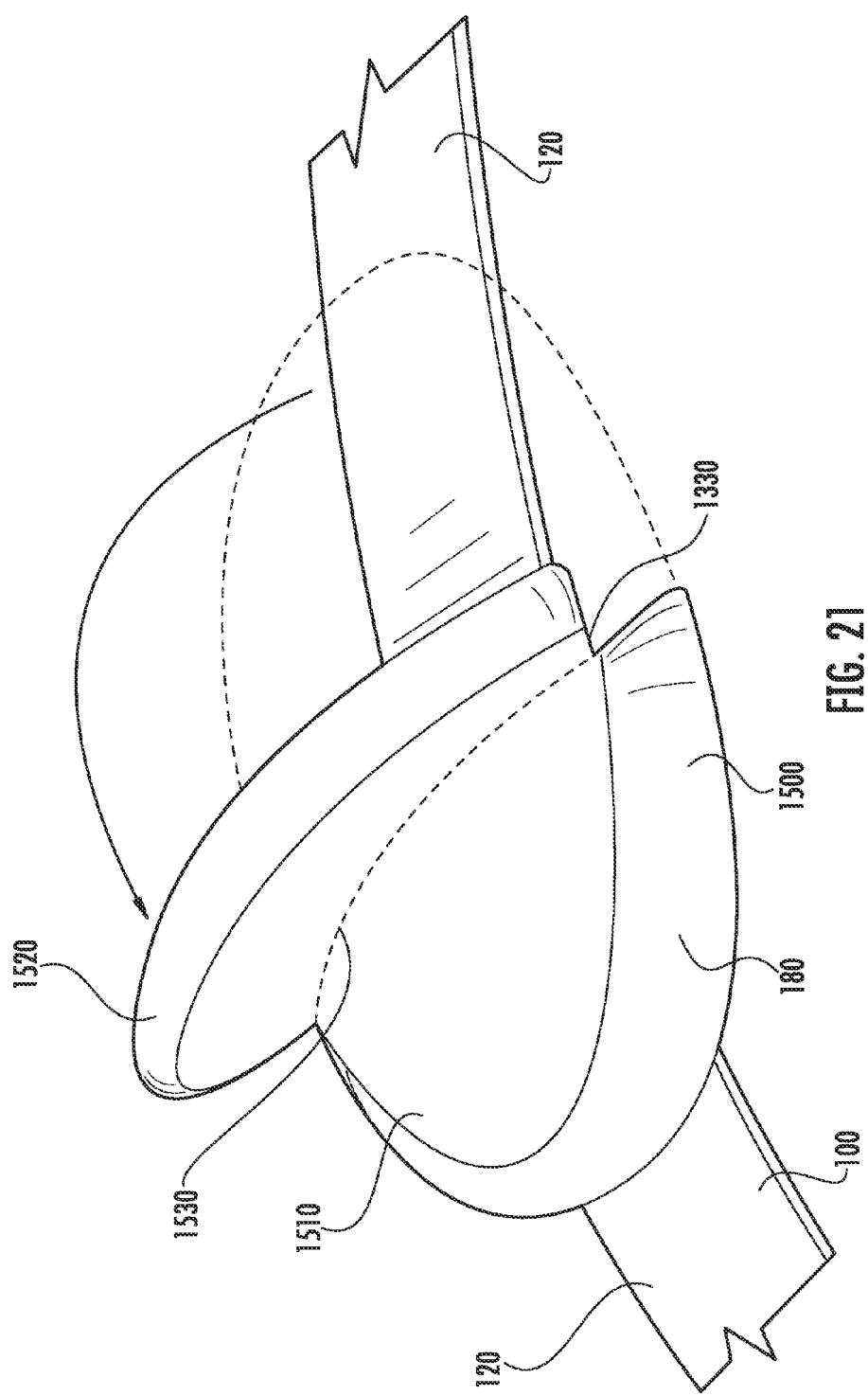

METHOD AND APPARATUS TO RELIEVE MENSTRUAL PAIN

CROSS-REFERENCE TO RELATED APPLICATIONS

This is a continuation-in-part of pending application Ser. No. 12/404,655 entitled "Method and Apparatus to Relieve Menstrual Pain" filed on Mar. 16, 2009, which in turn is a continuation-in-part of application Ser. No. 11/753,562 filed on May 24, 2007 (now abandoned), both of which are incorporated by reference herein.

FIELD OF THE INVENTION

The present invention relates to a method and apparatus to relieve menstrual pain. More specifically, the invention relates to a method and apparatus to relieve menstrual cramping through applying pressure to the exterior of the female body proximate to the hips.

BACKGROUND OF INVENTION

Menstrual cramping (dysmenorrheal) is a medical condition characterized by severe uterine pain during menstruation. The condition is the result of contractions of the uterus as it expels unneeded contents and also the passage of clotted blood through the cervix. The underlying pain results when the uterine muscles contract too hard or fast resulting in severe discomfort around the abdomen, back and often the legs.

The condition most commonly affects women between the ages of 20 through 24. While most women only experience minor pain during menstruation, menstrual cramps are often so severe as to limit normal activities or may require medication. Menstrual cramping may precede menstruation by several days or may accompany it. More typically, such cramping occurs on the first or second day of the menstrual cycle.

According to the United States Department of Health and Human Services, roughly 52 percent of women in the United States between the ages of 15 to 51 suffer from some level of menstrual cramps. Of these, 10 percent have such a severe condition as to require a doctor visit. Statistics from the American College of Obstetrics and Gynecology reveal that menstrual cramping represents the number one cause of missed school and work days among women. In fact, menstrual cramping accounts for an astonishing 140 million hours of lost school and work every year.

Despite these alarming statistics, very little has been done to advance the art of treating menstrual cramping. Traditional methods of chemical treatment include taking an over-the-counter pain killer which includes ibuprofen as the active ingredient. Non-traditional methods include a regiment of taking calcium, Vitamin D and magnesium supplements. Non-medicinal ways of treatment typically include use of heat around the abdomen, such as a heating pad or taking a warm sitz-bath.

Each aforementioned treatment option has its limitations, and none actually work to treat the underlying medical cause of these cramps. Studies show how increased ingestion of ibuprofen may result in multiple adverse drug reactions (ADRs), as well as associated gastrointestinal (GI) effects and renal problems. Many women cannot always take chemical medications due to these problems as well as other undesirable side affects. Dietary supplements like calcium, Vitamin D and magnesium may help reduce pain but do not eliminate or treat the condition. Use of heat around the abdomen only offers at most temporary relief and does nothing more than mask the pain.

With the growing acceptance of complementary and alternative medicine (CAD), there is a need in the art for an effective yet non-chemical treatment of menstrual cramps. This is especially true with the large number of individuals whose personal and spiritual beliefs preclude use of chemical medicines like ibuprofen.

SUMMARY OF THE INVENTION

This invention solves the current limitations in the art of alleviating menstrual cramps through an alternative and non-chemical form of treatment. As menstrual cramping occurs when the uterine muscles contract too hard or fast resulting in the various tissue connected to (or located near) the uterus to be stretched, the present invention treats the condition through counteracting this excessive stretching. Specifically, to relieve the pain and discomfort associated with menstrual cramping, the invention employs compression at or proximate to each greater trochanter—the large, irregular eminence located at the top of the femur bone—at both lateral sides of the female hips. Through compressing the area adjacent to each greater trochanter, the ligaments and tendons proximate to the uterus relax, helping alleviate the pain associated with menstrual cramps.

In the preferred embodiment, the apparatus may include one or more symmetrical tapered pads having an inner side and an outer side. Each outer side of each pad is semi-rigid while each inner side is flexible and compressible. The outer side of each pad is connected to one or more straps, each strap having a first end and a corresponding second end. A fastener is attached to the first end of each strap and a corresponding second fastener is attached to the second end of each strap. Both fasteners may be a buckle system, a latch system, Velcro or any other related locking system known in the art. In addition, a constricting device is located on or proximate to one pad sufficient to create a compression force through each strap when the first fastener and corresponding second fastener are connected to one another. Such constricting device may be a ratchet, pulley system, drum assembly or similar device known in the art.

In a second embodiment of the apparatus, the symmetrically tapered pads may be attached to one or more straps through a swivel bracket to vertically rotate the pad to conform with the user's hips.

In a third embodiment of the apparatus, an inner bladder system may supplant the flexible and compressible inner side of the pads. The inner bladder may be filled with a gas or liquid sufficient to conform to the user's hips.

In a fourth embodiment, the apparatus may have one or more symmetrically tapered pads, each having an outer side and an inner side. The outer side of each pad is affixed to the inner side of a C-shaped belt. In addition, the C-shaped belt may include a constricting device, which may include, but is not necessarily limited to, a spring-member (and/or screw based system attached to each pad) sufficient to compress each symmetrically tapered pad onto the greater trochanters of the user.

In a fifth embodiment, the apparatus may include a variable compression drive capable of accurately compressing both the left pad and right pad onto the greater trochanters of the user. Such variable compression drive may include an outer drum shell which attaches to the strap, as well as an inner rotator having an inner diameter that is treaded. Here, the inner rotator is shaped to fit within the outer drum shell. A motor powers the inner rotator. The compression drive further includes a threaded shaft having a first end and a second end, where the threaded shaft has a sufficient dimension so as to engage the inner diameter of the inner rotator. A tab positioned on the strap helps engage the second end of the threaded shaft.

Furthermore, the apparatus may include a controller assembly to help automate the apparatus and ensure proper use. The controller assembly may include a central controller attached to the strap in communication with the variable compression drive. Such central controller may have an essentially rectangular housing which includes a front display and a plurality of buttons. Positioned within the rectangular housing is a processor and memory device powered by a self contained power source (which can be a battery). The memory device may store computer programs in the form of machine readable code.

Moreover, the central controller may include an uplink (a USB or antenna) sufficient to connect the memory device to report performance data to an outside computing device (such as a smart cellular telephone, a PDA, a table computer, laptop or similar computer). Accordingly, the central controller may communicate with a pressure sensor attached to the variable compression drive to post the compression force on the front display. In addition, a computer program may send an alert to the variable compression drive to reduce the compression force should the pressure sensor determine that such compression is above a threshold value.

Optionally, one or more pads of the apparatus may include a customizable therapy assembly, in order to provide hot or cold therapy in addition to compression. Such assembly may include a female holder and a removable male heat pad (which can be any form of therapy, not just limited to heat), where the female holder is essentially elliptical and includes an outer ring and a cavity sufficient to receive the male heat pad. The male heat pad may have a sufficient size and dimension to be locked within the cavity of the female holder. As such, the male heat pad may have an exterior sleeve filled with a gel or liquid capable of conducting heat. Such therapy pad can vary in density to regulate the level of pressure to conform to varying user preferences. Moreover, such therapy pad can vary in both geometry and malleability to allow application for a variety of body types. Such malleability may be induced by heat, chemical reaction or similar method.

The preferred embodiment of the method may include the steps of placing one or more pads proximate to the greater trochanters of a user; affixing each pad to one or more straps where each strap has a first end and a second end at the opposite portion of each strap; connecting the first and second end of each strap through a fastener, and creating pressure sufficient to compress each pad onto the user. Under this preferred method, 10 to 15 pounds of pressure is administered for between 5 to 10 minutes after the user reports the menstrual pain has subsided.

The method may also include the additional steps of shaping each pad to conform with the shape of the user's hip(s), as well as vertically rotating each pad through a swivel bracket into a position which further conforms with the shape of each hip. The systems and methods described herein are meant to not only treat menstrual cramping but also to provide relief from more minor episodes of menstrual pain and discomfort.

Upon treatment by the apparatus, the method may further contemplate post-treatment through use of a compression undergarment that includes one or more compression belts. The compression undergarment may take the form of a skirt, shorts or spanx and may include a first annular sleeve and second annular sleeve positioned at the sides of the undergarment (proximate the user's hips). Both annular sleeves may include a top opening and cavity which form a pocket. A first pad can be inserted into the first annular sleeve while a second pad may be inserted into the second annular sleeve. One or more compression belts can then be placed over the compression undergarment to secure and maintain both the first pad and second pad within both annular sleeves. Such compression belts may have varying elasticity to conform to the level of menstrual cramping of the user.

Accordingly, post treatment via the compression undergarment may include placing the first pad into the first annular sleeve, then placing the second pad into the second annular sleeve. Next, both pads should be aligned within each sleeve so they will be located proximate the user's greater trochanters. Next, one or more compression belts are positioned on top of the compression undergarment to cover both annular sleeves to maintain both the first pad and second pad as well as provide compression. The post-treatment method next contemplates placing the compression undergarment and corresponding compression belt onto the user for a period of time not to exceed eight hours. As a second embodiment of the compression undergarment, such device can simply be the undergarment (in the form of spanx, shorts or similar clothing article) that includes a compression belt positioned proximate the user's hips to allow for some level of compression. As yet another embodiment, the undergarment (without any form of cavity/pocket for insertion of pads) may simply include a series of grids proximate the hips. The user can dawn such undergarment so as to properly locate the user's greater trochanters (via positioning aids in the form of grids), so as to properly place both the left pad and right pad of the apparatus.

BRIEF DESCRIPTION OF THE DRAWINGS

For a fuller understanding of the invention, reference is made to the following detailed description, taken in connection with the accompanying drawings illustrating various embodiments of the present invention, in which:

FIG. 2A illustrates a left perspective view of the apparatus;

FIG. 2B illustrates a right perspective view of the apparatus;

FIG. 6 illustrates a partially cut away top view of the apparatus;

FIG. 7 illustrates a perspective view of the left pad of the apparatus showing how the left pad can be rotated;

FIG. 8A illustrates an exploded view of the left pad of the apparatus;

FIG. 8B illustrates a further exploded view of the left pad of the apparatus;

FIG. 10A illustrates an exploded view of the right part of the apparatus;

FIG. 10B illustrates a further exploded view of the right part of the apparatus;

FIGS. 13(a) and 13(b) show a perspective view of two embodiments of a constricting device. FIG. 13(a) illustrates a ratchet system, while FIG. 13(b) illustrates a pulley system;

FIGS. 14(a) and 14(b) show two different embodiments of the two-part construction for each pad. FIG. 14(a) is an exploded view of a two-part construction having a semi-rigid outer side and a flexible and compressible inner side. FIG. 14(b) illustrates the two-part construction having a semi-rigid outer side and an inner bladder system;

FIG. 15 illustrates a perspective view of the front of a pad having symmetrically tapered portions;

FIG. 18(b) illustrates the central controller which includes a memory device, processor and power source;

FIG. 19 illustrates one form of pneumatic pad having a bladder that can be automatically inflated via piston;

FIG. 20 illustrates an alternative form of pad that includes a cavity to receive a sleeved heated therapy pad;

FIG. 21 is a perspective view of a travel pad having a crease which folds;

DETAILED DESCRIPTION OF THE INVENTION

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout.

Figure 1A:
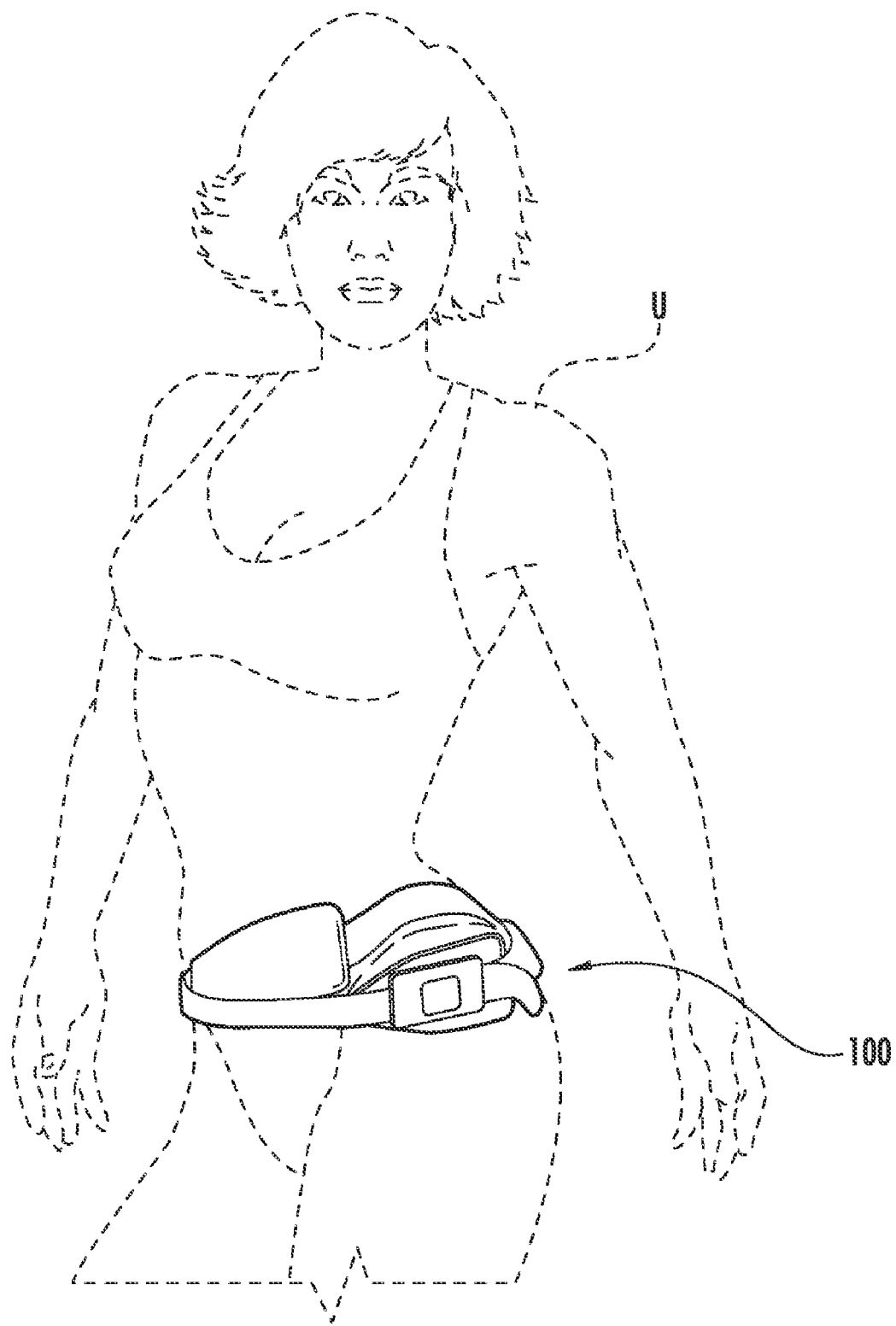
FIG. 1A is a perspective environmental view of an apparatus to treat menstrual cramping according to one embodiment of the present invention.

The present invention relates to a method and apparatus to non-chemically relieve menstrual cramping through use of compression at or proximate to the greater trochanters. Throughout the embodiments described below, an apparatus to treat menstrual cramping is denoted by the numeric label 100 as shown in FIG. 1A.

Figure 1B:
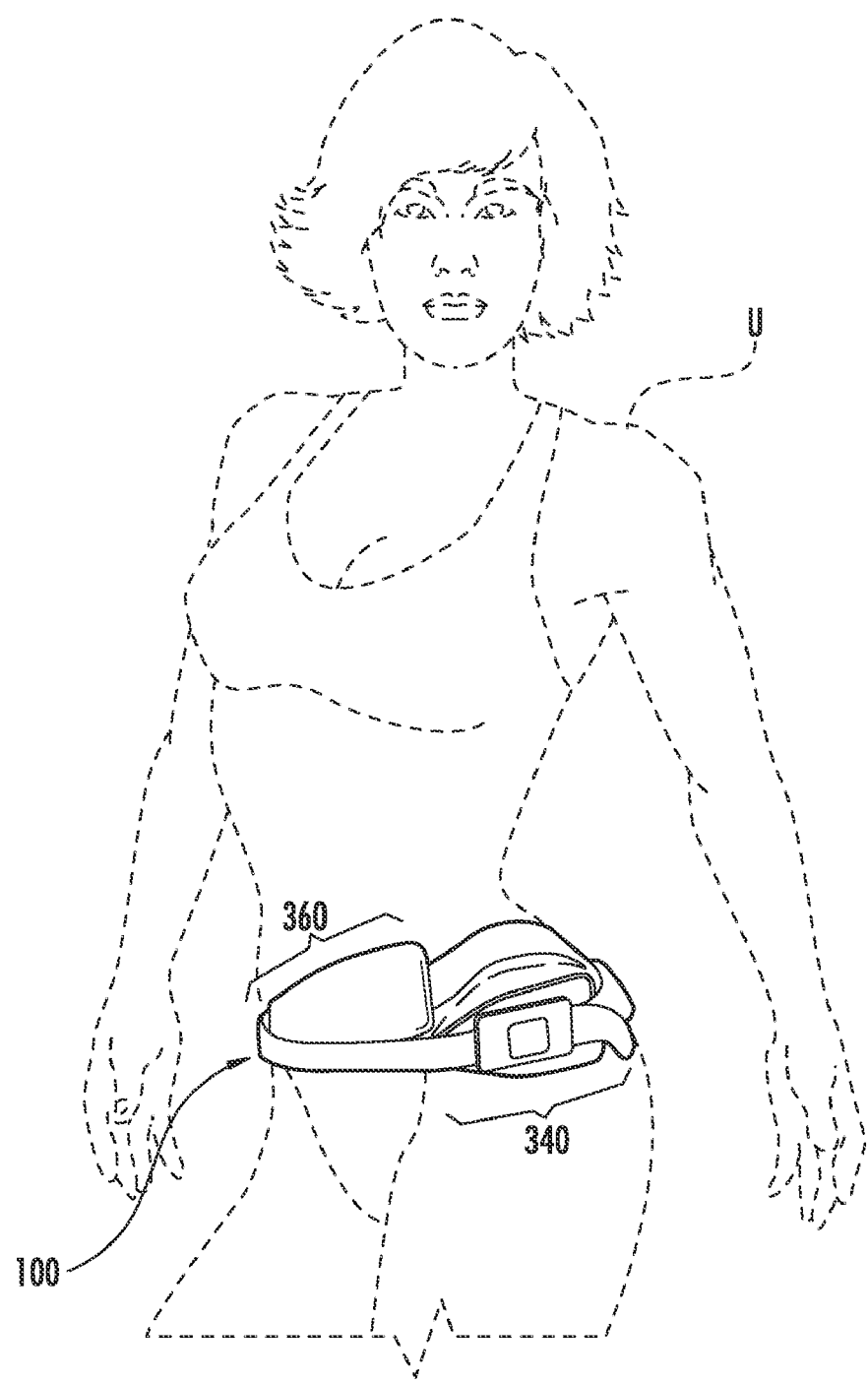
FIG. 1B is a further perspective environmental view of the apparatus to treat menstrual cramping of FIG. 1A.

The typical cause of menstrual cramping is excessive stretching of the muscles and tendons surrounding the uterus when expelling unwanted materials on the inner uterine wall during menstruation. When these muscles contract too fast or hard, it results in stretching of tissue resulting in the pain and discomfort associated with menstrual cramping. FIG. 1B illustrates how the apparatus 100 includes a left pad member 340 and a right pad member 360 laterally placed at each side of the user's (U) body near or proximate to the hips. By placing both pad members 340 and 360 proximate to the greater trochanters (located below the hips) and creating sufficient compression, the apparatus 100 decreases the stretching of tendons and ligaments surrounding the uterus, thus relaxing the tissue and alleviating cramping after a period of time and regiment of use.

A more detailed view of the individual components of one embodiment of apparatus 100 is offered by FIG. 2A. The apparatus 100 includes one or more essentially planar pads, preferably a left pad 180 and right pad 200. When assembled in the apparatus 100, each pad 180 and 200 provides a vertical surface for contact with the lateral sides of the user's (U) body proximate to the hips.

Each pad 180 and 200 is preferably made of two-part construction which includes a semi-rigid or hard outer side 680 and a more flexible and compressible inner side 620 (described in FIG. 6 below). In addition to at least one pad 200, the apparatus 100 also comprises one or more straps 120, each having an inner side 300 and an outer side 320. Each strap 120 likewise has a first end 280 and a corresponding second end 260 (shown in FIG. 6) connected to each other via a fastener 140.

In the embodiment shown in FIG. 2A, the fastener 140 is a push-button release type system located at or proximate to the left pad 180. However, such fastener 140 can be located anywhere along the circuit of the apparatus 100. Here, the push button fastener 140 has an exterior side 380, an interior side 400 (described in FIG. 8B below), a first end 420 and a second end 440. The fastener 140 is attached to the outer side 320 of the strap 120. While a push-button type system is one means for securing the first end 280 and corresponding second end 260 of the strap 120, any other acceptable fastening system may be used. This can include a latch system, a buckle system, Velcro, or any fastening system known to those skilled in the art.

FIG. 2B provides another perspective of the apparatus 100 illustrated in FIG. 2A, showing a more detailed assembly of the right pad member 360. In this embodiment, the strap 120 connects to the right pad member 360 through a sleeve 160 of sufficient shape and size as to receive the strap 120. The invention is not restricted to use of a sleeve 160 to connect each pad member 340 or 360 to the one of more straps 120 of the apparatus 100. Rather, one of ordinary skill in the art can use any known system to affix or connect each strap 120 to each pad member 340 or 360. However, it is preferable that such system allow at least one pad 180 or 200 to move along the circuit of the strap(s) 120 sufficient to place properly place both pads 180 and 200 proximate to the user's (U) hips.

Figure 3:
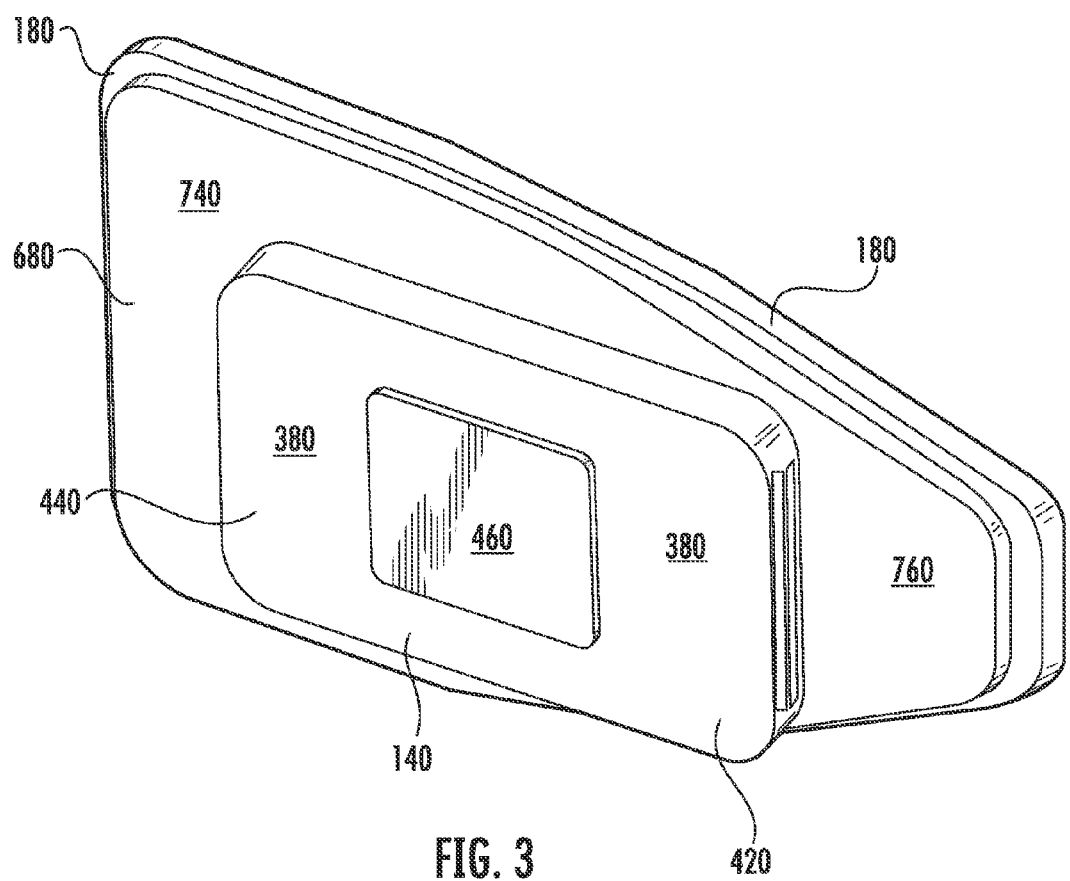
FIG. 3 illustrates a perspective view of the left part of an apparatus of FIG. 2A.

A more detailed perspective of the left pad 180 and fastener 140 is provided in FIG. 3. As illustrated, each pad has a front portion 760 and a rear portion 740. While the illustrated shape of each pad 180 (and 200) is tapered from the rear portion 740 to the front portion 760, a variety of shapes may be used based upon the user's (U) preference. One preferred shape is where both the rear portion 740 and front portion 760 are symmetrically tapered from the center of the pad 180 (as shown in more detail in FIG. 15 below). The invention also contemplates creating a mold of the user's (U) hips sufficient to create a custom shape for both the left pad 180 and right pad 200. The invention further contemplates making the outer side 680 of each pad 180 and 200 of a sufficiently malleable and formable material which can be formed to mirror the unique shape of the user's (U) hips.

Figure 4:
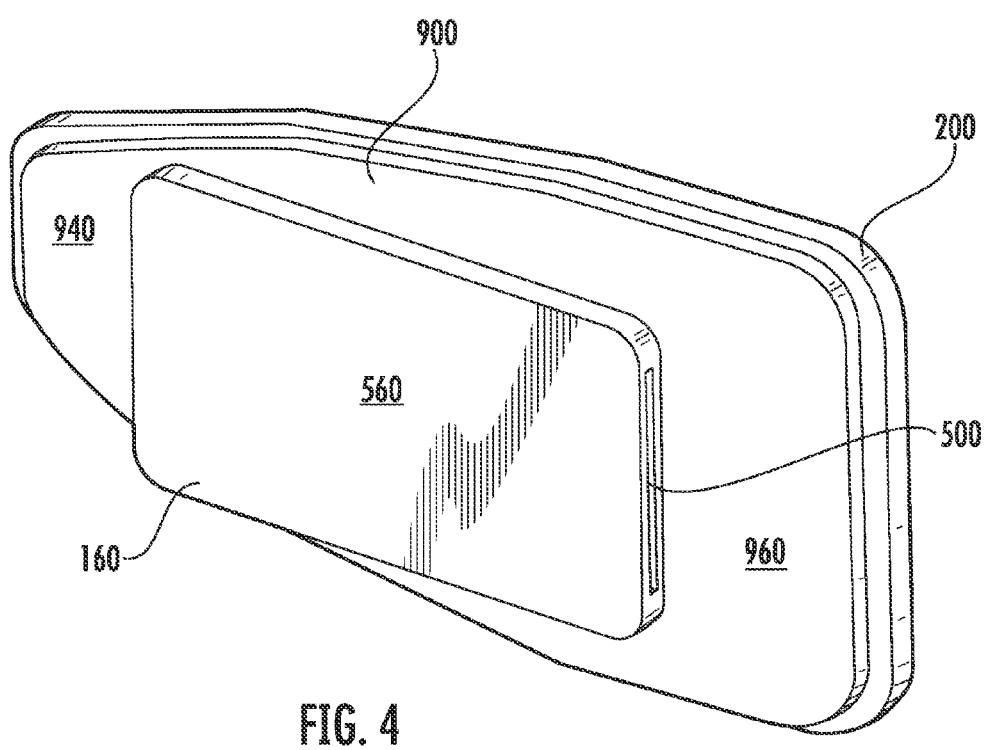
FIG. 4 illustrates a perspective view of the right part of the apparatus of FIG. 2B.

FIG. 4 provides a more detailed illustration of the right pad 200 and sleeve 160. Similar to the left pad 180, the right pad 200 has a front portion 940 and a rear portion 960. Likewise, the right pad 200 tapers from the rear portion 960 towards the front portion 940. Again, the sleeve 160 is shaped to have a bore-through hollow opening 500 of sufficient size and shape as to receive one or more straps 120. As discussed in more detail below in FIGS. 13(a) and 13(b), the present invention includes (in addition to the fastener 140) a constricting device 1100 to be located on or proximate to a pad 200. The constricting device 1100 can be a ratchet, pulley system or any similar mechanism which creates compression known to those ordinarily skilled in the art.

Figure 5:
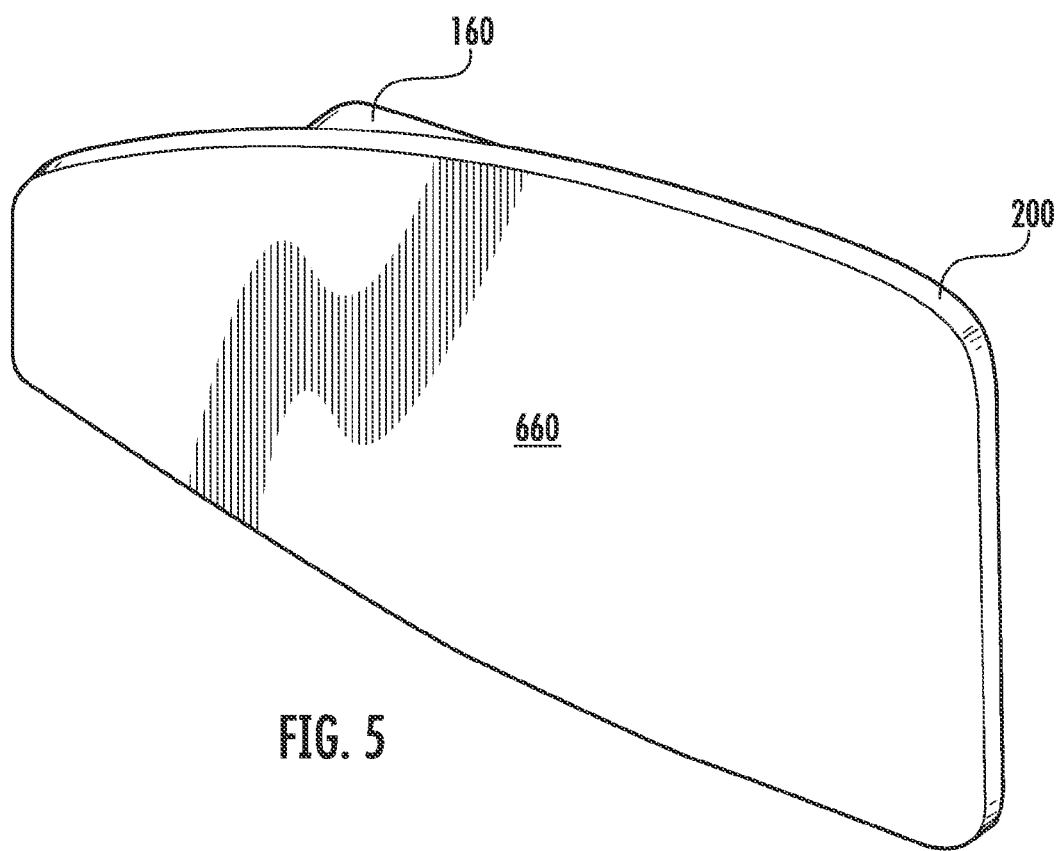
FIG. 5 illustrates a perspective view of a right pad of the apparatus.

A more detailed view of the inner side 660 of the right pad 200 is offered by FIG. 5. As the inner side 660 has direct contact with the user's (U) hips, it should be made of foam, neoprene or another compressible and hypoallergenic material known by those skilled in the art. It is also preferred that each pad 180 and 200 includes an outer housing 161 (shown in FIG. 14(b) and described below) to maintain the components of each pad, including the semi rigid outer side 680 and inner side 660. Such outer housing 161 should be washable and also hypoallergenic.

In addition to the malleable properties of each pad's two-part construction, one embodiment of the apparatus 100 includes use of vertical rotatable members to connect the strap(s) 120 to each pad 180 and 200, to greater conform to the individual shape of each user's (U) hips. FIG. 6 offers a partial cut away top view of both the left pad member 340 and right pad member 360, which includes these vertical rotatable members. The right pad member 360 illustrated in FIG. 6, includes a right pad 200 comprising a front portion 940 and a rear portion 960, which includes a semi-rigid outer side 900 and a flexible and compressible inner side 660. Located at the center of the semi-rigid outer side 900 of the right pad 200 is a female receiving notch 980 for use in connecting the sleeve 160 with a rotatable male swivel bracket 920 having an upper wall 1000. The female receiving notch 980 has a cavity 692, created by a flat upper wall 690 parallel with the semi-rigid outer side 900 of the right pad 200, sufficient to receive the rotatable male swivel bracket 920. The sleeve 160 is affixed to the upper wall 1000 of the rotatable male swivel bracket 920 to ultimately connect with the right pad 200 to form the right pad member 360. As illustrated, the sleeve 160 has a front portion 540 and a rear portion 520, and an outer side portion 560.

FIG. 6 also provides a more detailed view of the components of the left pad member 340, which in this embodiment positions the fastener 140 on the left pad 180. Just as with the right pad 200, the left pad 180 includes a semi-rigid or hard outer side 680 and a more flexible and compressible inner side 620. Attached to the semi-rigid outer side 680 is a female receiving notch 592, capable of receiving a rotatable male swivel bracket 700 having an upper planar member 720 and a lower planar member 730 connected to interior side 400 of the fastener 140. The fastener 140 depicted in FIG. 6 has an exterior side 380, a first end 420, a second end 440, and a push button 460 to release the first end 280 of the strap 120. The second end 260 of the strap 120 is attached to the fastener 140 at or near its first end 420. Release of the first end 280 of the strap 120 is achieved through a spring-action member 480.

FIG. 7 illustrates how the embodiment show in FIG. 6 allows the left pad 180 to rotate into a position which conforms with the user's (U) unique hip shape.

FIG. 8A is an exploded view of the left pad 180 shown in FIGS. 6 and 7. As shown, the fastener 140 having a push button release 460 is connected to the left pad 180 at its interior side 400 to the lower planar member 730 of the swivel bracket 700. Here, the bracket is a circular disc 800, which attaches to a corresponding circular recess 590 located on the semi-rigid outer side 680 of the left pad 180. The semi-rigid outer side 680 then connects to the flexible and compressible inner side 620 at its outer portion 600. Combination of the swivel bracket 700 and both the inner 620 and outer 680 sides of the left pad 180 comprise the left swivel member 220 of the apparatus 100. FIG. 8B represents a 180 degree view of the left pad 180 shown in the exploded view of FIG. 8A.

Figure 9:
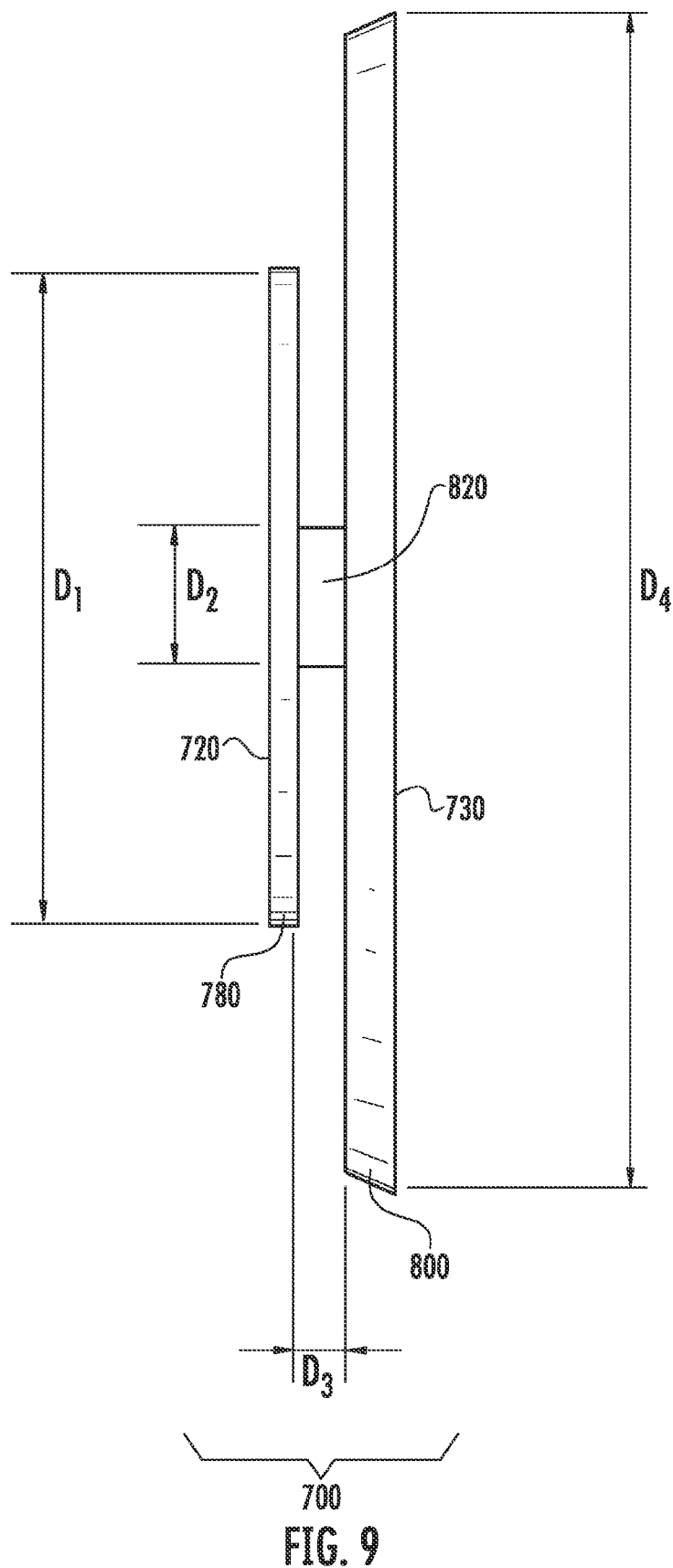
FIG. 9 illustrates a side view of the secondary left swivel-bracket.
Figure 9B:
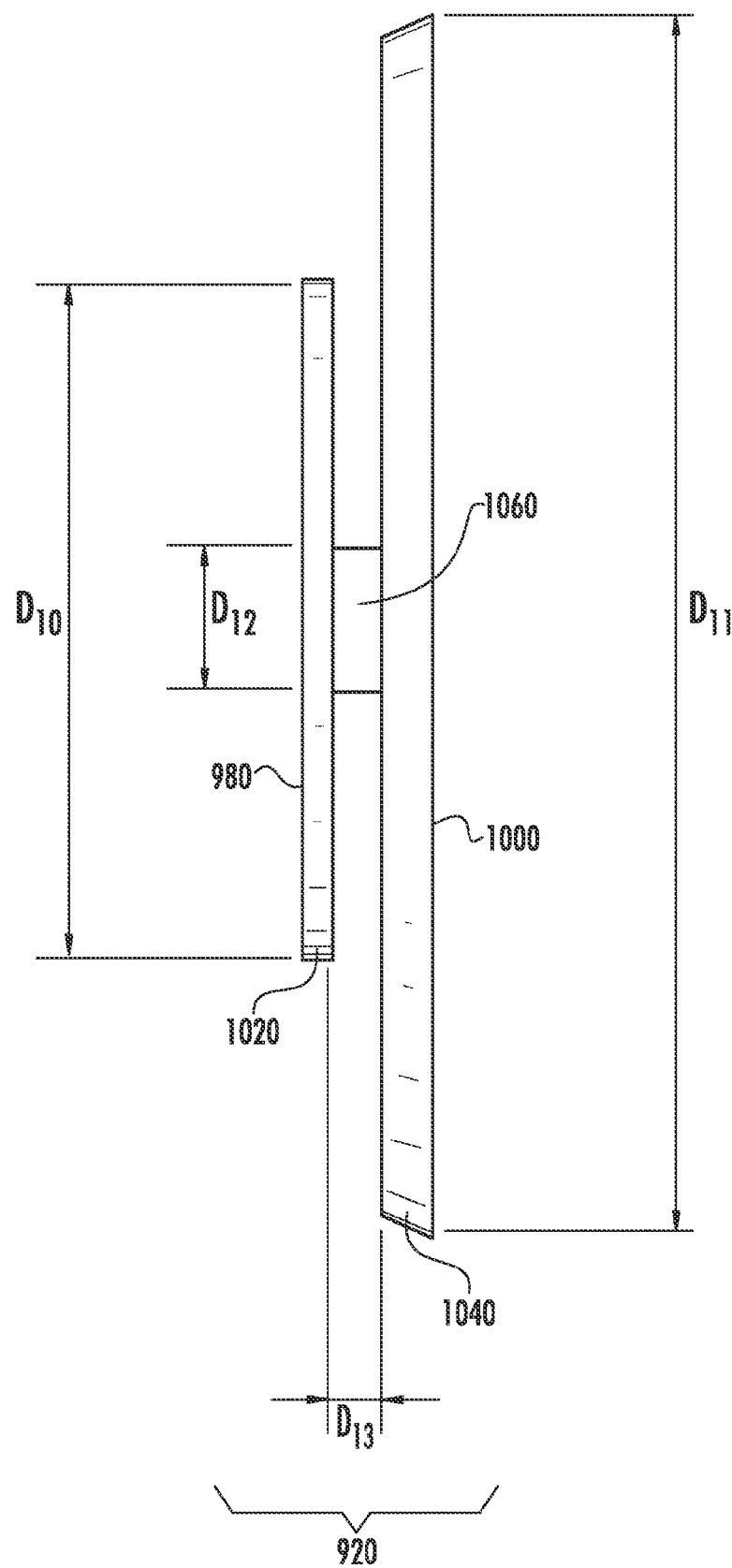
FIG. 9B illustrates a side view of the secondary right swivel-bracket.

Detailed description of FIGS. 9 and 9B are incorporated by reference from the parent application.

FIG. 10A is an exploded view of the right pad 200 of FIG. 6. Here, the sleeve 160 connects with the circular bracket 920 at the sleeve's 160 back portion 580. The circular bracket 920 is of two-part construction having a larger circular outer ring 1040 and a smaller circular inner ring 1020. The smaller circular inner ring 1020 connects with exterior side 900 of the right pad 200 at its upper side 980. FIG. 10B represents a 180 degree view of the right pad 200 shown in the exploded view of FIG. 10A.

Figure 11:
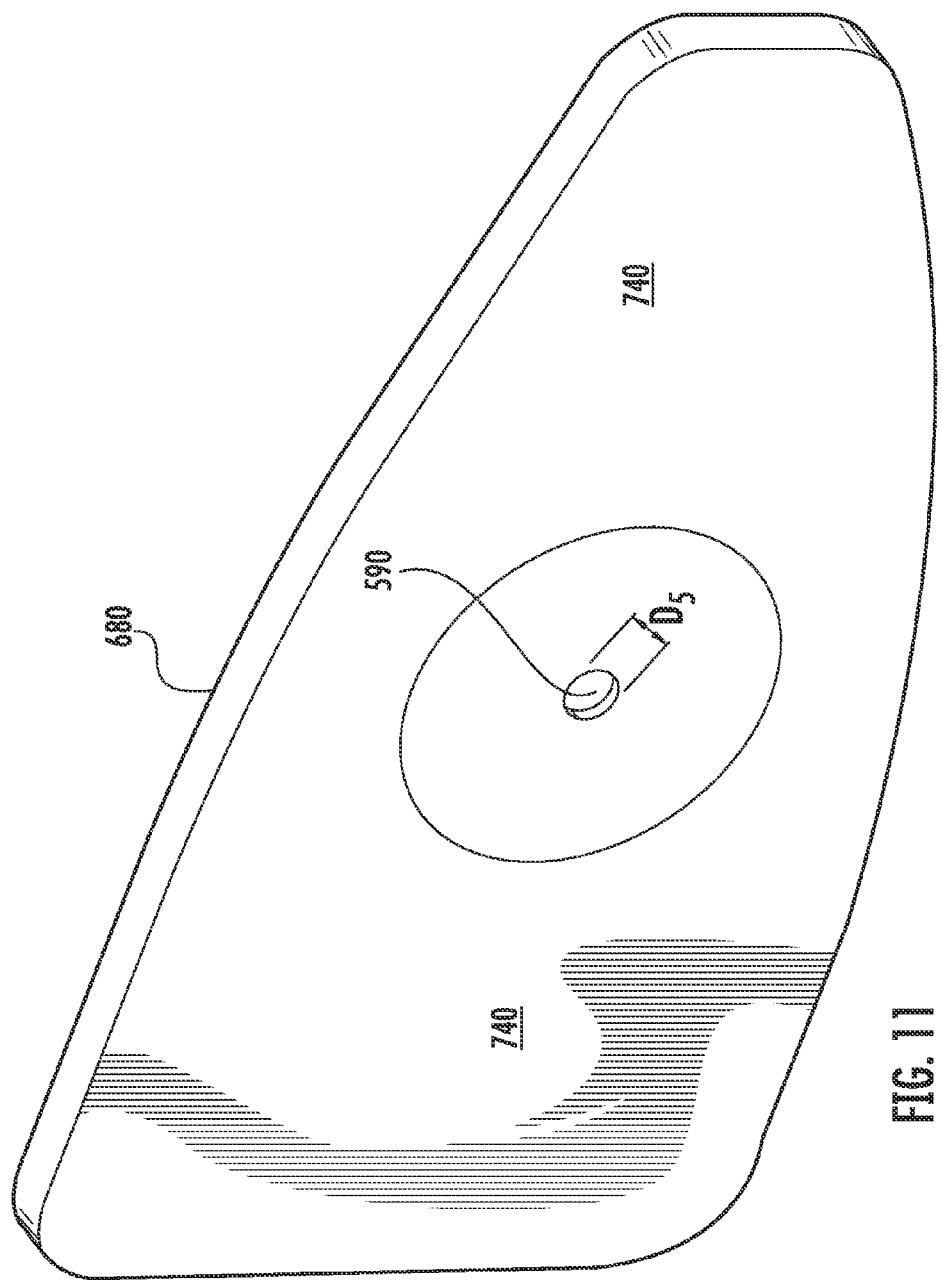
FIG. 11 illustrates a view of the primary left swivel bracket.
Figure 12:
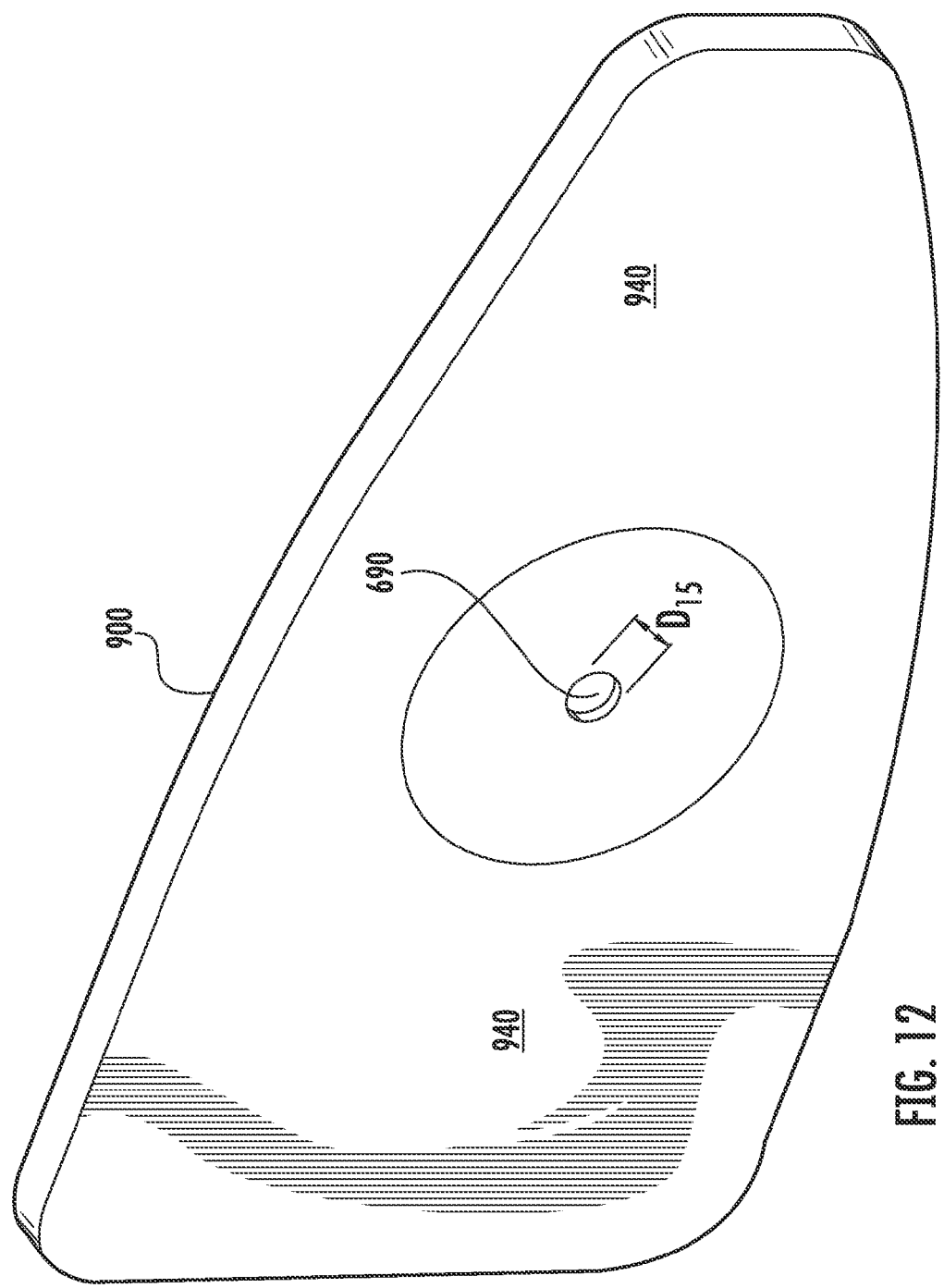
FIG. 12 illustrates a view of the primary right swivel bracket.

FIGS. 11 and 12 both offer perspective views how the semi-rigid outer members 680 and 900 of the left pad 180 and right pad 200 connect with the smaller circular inner rings 1020 of each swivel bracket 920. FIG. 11 illustrates how the left pad 180 includes a recess 590 of sufficient size and dimension to receive the smaller circular ring 1020 of the swivel bracket 920. Likewise, FIG. 12 illustrates a similar recess on the flat upper wall 690 of the semi-rigid outer side 900 of the right pad 200 sufficient to receive the rotatable male swivel bracket 920.

Figure 13A:
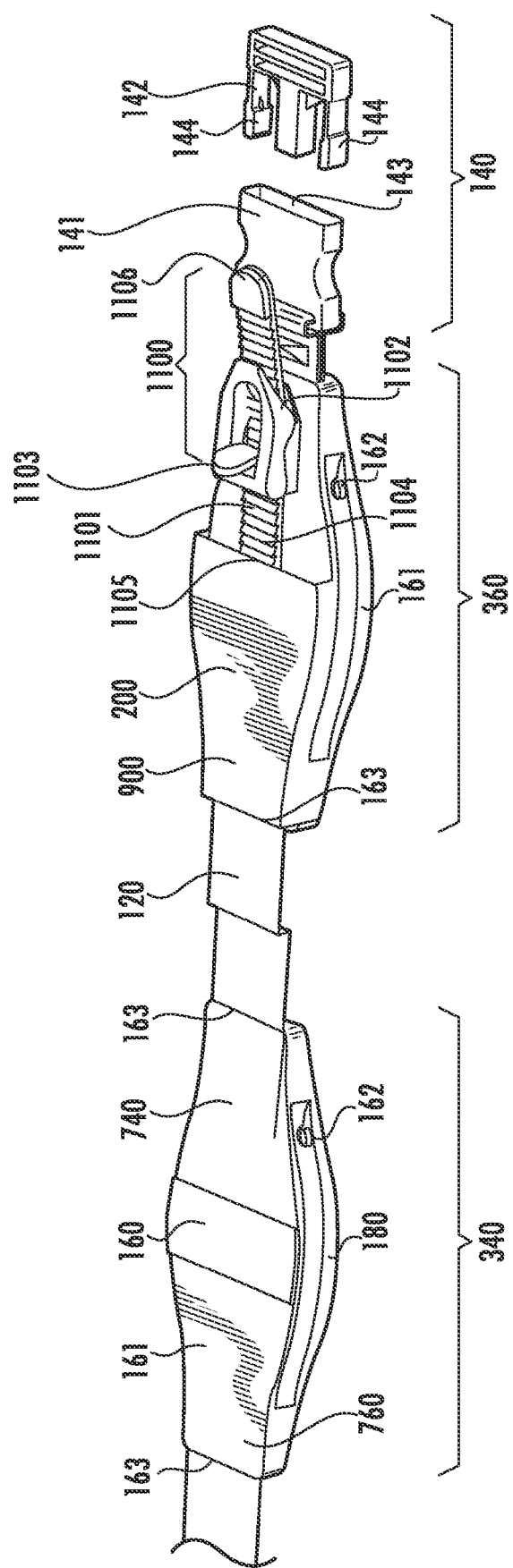

FIGS. 13(a) and 13(b) are perspective views of two different embodiments of the constricting device 1100 affixed to the right pad 200. FIG. 13(a) illustrates the fastener 140, as a buckle system, having a first fastener 141 and a corresponding second fastener 142. The first fastener 141 has an opening 143 of sufficient size and dimension to receive the one or more flexible prongs 144 of the corresponding second fastener 142.

The constricting device 1100 illustrated in FIG. 13(a) is a ratchet, having a ratchet strap 1101 with multiple teeth 1104, which is fed into a locking member 1102. The locking member 1102 is connected the semi-rigid outer side 900 of the right pad 200. The ratchet strap 1101 has a back portion 1105 and front portion 1106. The back portion 1105 is connected to the first end 280 of the strap(s) 120. The locking member 1102 includes a rotatable handle 1103, which rotates back and forth sufficient to pull the teeth 1104 of the ratchet strap 1101 to tighten, as well as release to reduce and/or eliminate compression. Both the right pad 200 and left pad 180 of the embodiment are encased by an outer housing 161 secured by a zipper system 162.

Another embodiment of the constricting device 1100 is the pulley system shown in FIG. 13(b). This pulley system is connected to the semi-rigid outer side 900 of the right pad 200. Here, the constricting device 1100 is comprised of multiple strings 1110 connected to the first end 280 of the strap(s) 120. Each of the strings 1110 pass through a rigid pulley chamber 1111, and connect to a circular spindle 1112. Affixed to the top of the spindle 1112 is a rotatable exterior handle 1113. Through the mechanical advantage of twisting the strings 1110 around the spindle 1112, the strings 1110 are pulled into the rigid pulley chamber 1111, which in turn constricts the strap(s) 120.

The Multi-Layer Pad

Figure 14A:
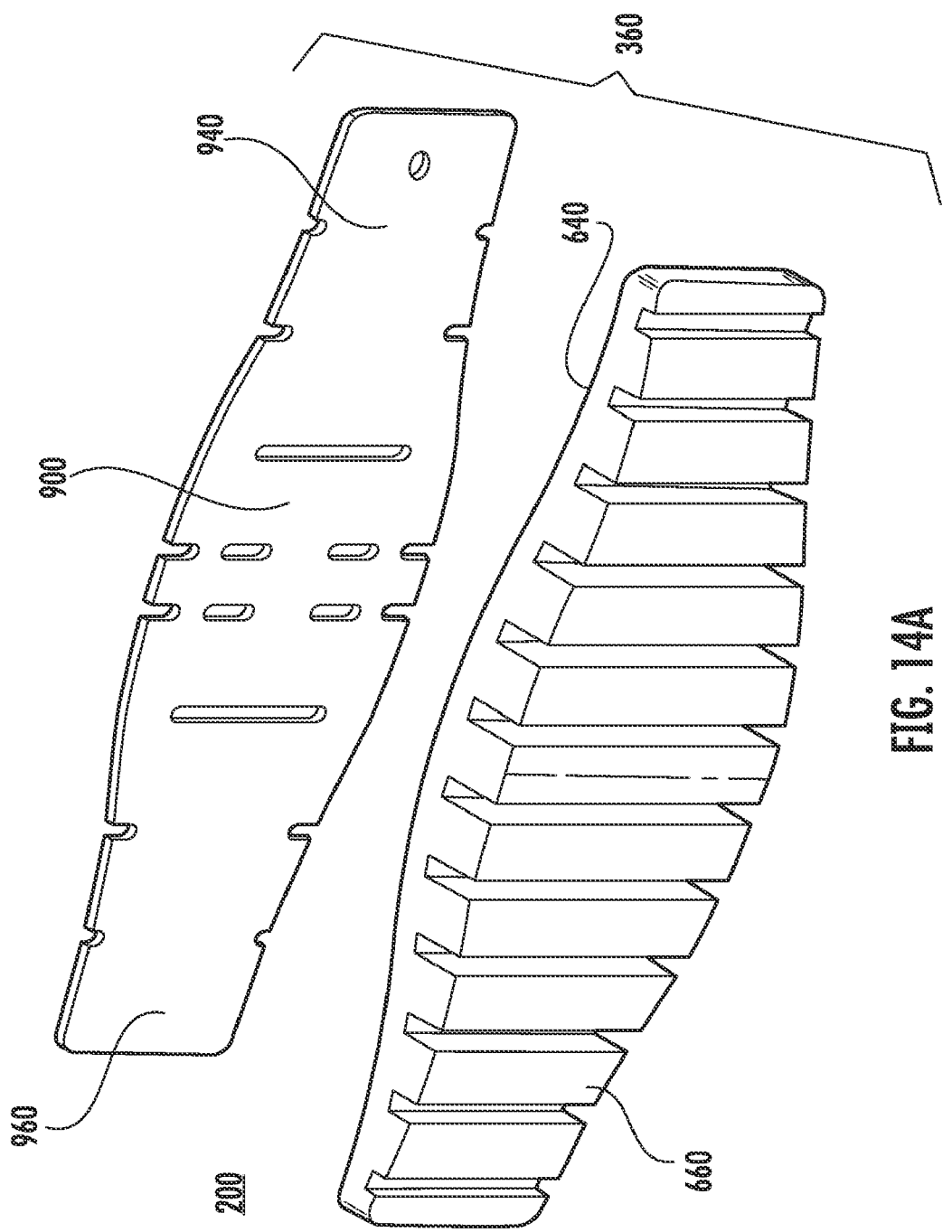

FIGS. 14(a) and 14(b) illustrate two different embodiments of the two-part construction of the pad 200. FIG. 14(a) is an exploded view showing how the pad member 360 includes a semi-rigid outer side 900 and a flexible compressible inner side 660. The semi-rigid outer side 900 has a front portion 940 and rear portion 960 and rests on the back 640 of the compressible inner side 660. The semi-rigid outer side 900 can be affixed to the strap(s) 120. The flexible compressible inner side 660 has a uniform stepped shape, such that when the apparatus 100 is compressed, the pad 200 can flex inward.

FIG. 14(b) illustrates another two-part construction for the right pad member 360. Here, the flexible compressible inner side 660 of the pad 200 is a liquid or gas filed inner bladder 661. The amount of liquid or gas which is placed in the inner bladder 661 can be adjusted to the user's (U) individual preferences. The inner bladder 661 is positioned or affixed on the semi-rigid outer side 900 of the pad 200. An outer housing 161 of sufficient size and dimension can be placed around both the bladder 661 and semi-rigid outer side 900, which can be closed via a zipper system 162. The housing 161 also contains a left and right opening 163 of sufficient size and dimension to allow the strap 120 to pass through and/or be affixed to the semi-rigid outer side 900.

FIG. 15 illustrates a perspective of the left pad 180, where both the rear portion 740 and front portion 760 are symmetrically tapered from the center.

Figure 16:
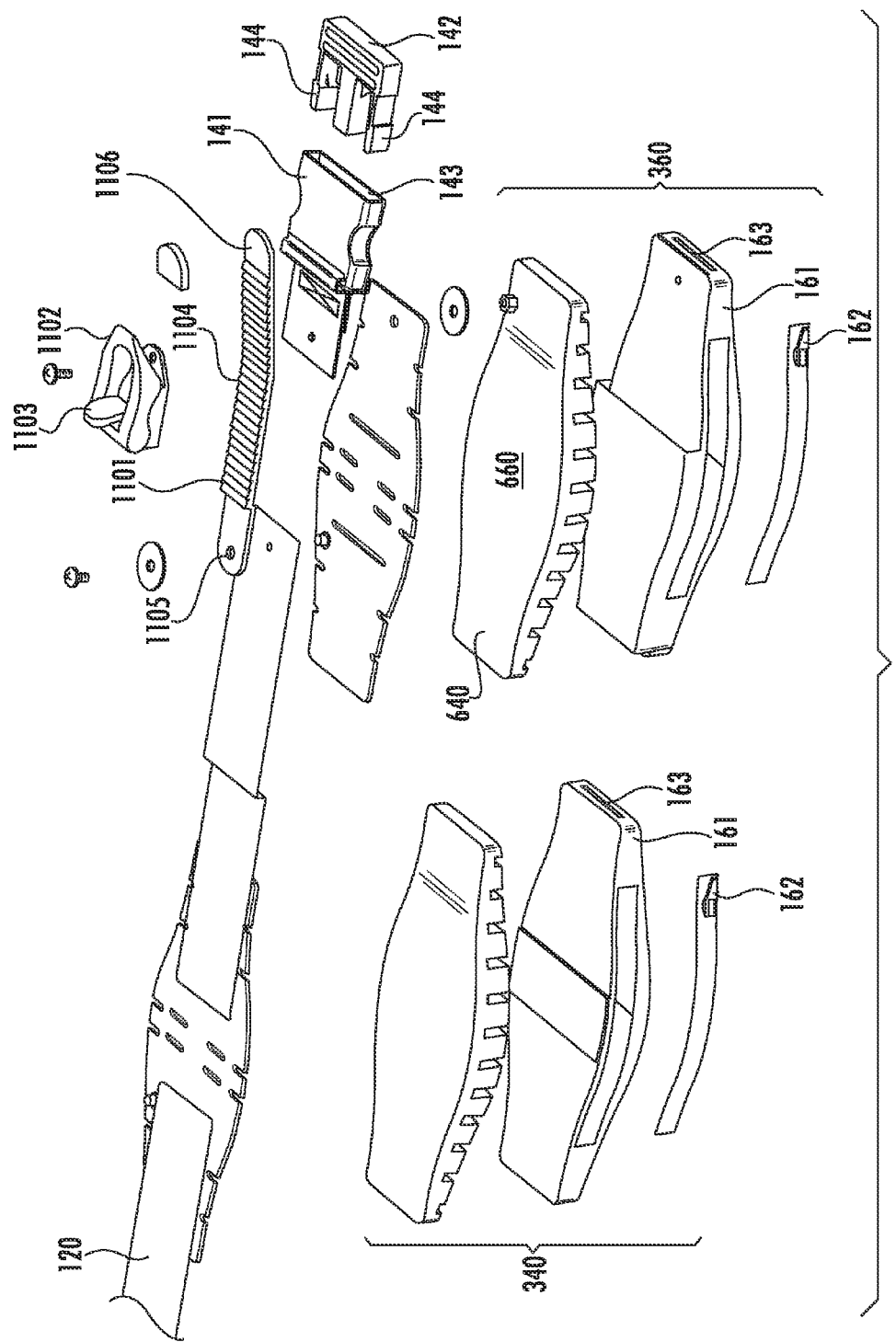
FIG. 16 illustrates an exploded view of one embodiment, which includes a ratchet as the constricting device.

FIG. 16 offers an exploded view of the components of the apparatus 100, where the constricting device 1110 is a ratchet. The embodiment illustrates how both the left pad 180 and right pad 200 are each placed into an outer housing 161. Each housing 161 has opening on both the right and left sides of sufficient size and dimension to allow the strap 120 to pass through. In this embodiment, the strap 120 is affixed to the left pad 180 and right pad 200. Each sleeve 160 is placed around the flexible compressible inner side 660, the semi-rigid outer side 900, as well as the strap 120, and secured by closing the zipper system 161. Here, the right pad member 360 is attached to the locking member 1102. The back portion 1105 of the ratchet strap 1101 connects with the first end 280 of the strap(s) 120. When the rotatable handle 1103 pivots back and forth, it engages the teeth 1104 of the ratchet strap 1101, which causes the apparatus 100 to compress.

The C-Shaped Belt Assembly

Figure 17:
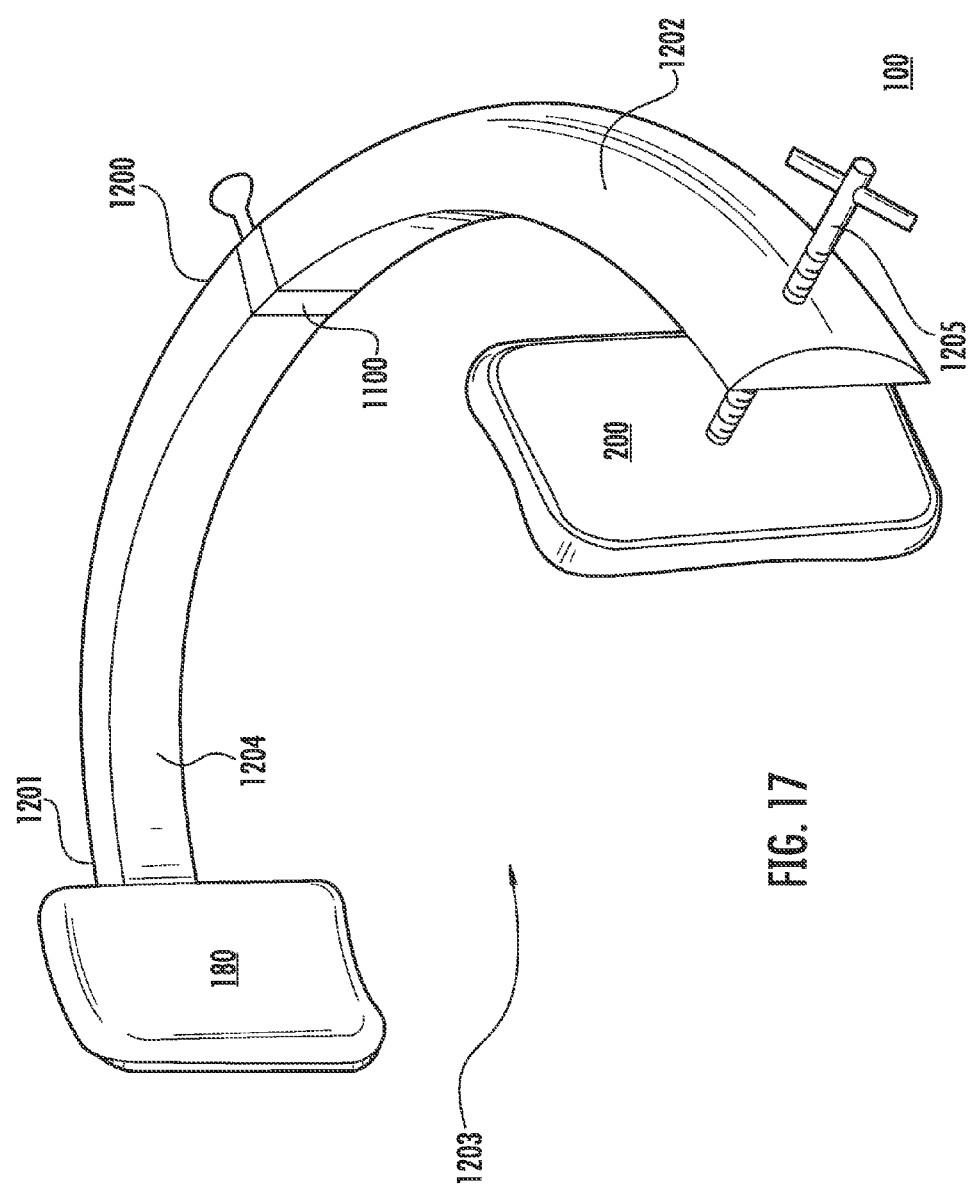
FIG. 17 illustrates a perspective view of another embodiment of the apparatus having a rigid C-shaped belt.

FIG. 17 illustrates an alternative embodiment of the invention where the strap 120 and fastener 140 described above is replaced by a rigid C-Shaped belt 1200. The belt 1200 has a first end 1201 and a corresponding second end 1202, with an opening 1203 of sufficient size and dimension to allow the belt 1200 to be placed around the user (U)'s hips.

The apparatus 100 can include (but does not necessarily require) a compression device 1100, such as a spring, at or proximate to the center of the belt 1200 to create an internal compression force. At the inner side 1204 of the belt 1200, a left pad 180 and right pad 200 are attached. Here, the compression device 1100 can also be a screw based system 1205 to twist both pads 180 and 200 in place and to create a sufficient compression force onto the user's hips proximate to each greater trochanter. Under such a system, each pad 180 and 200 can be vertically rotated via the screw based system 1205 to conform to the individual user's hips and preference. Other systems, known to those ordinary skilled in the art, can be used to attach the pads 180 and 200 to the belt 1200 and to be compressed onto the user's (U) hips.

The Controller

Figure 18A:
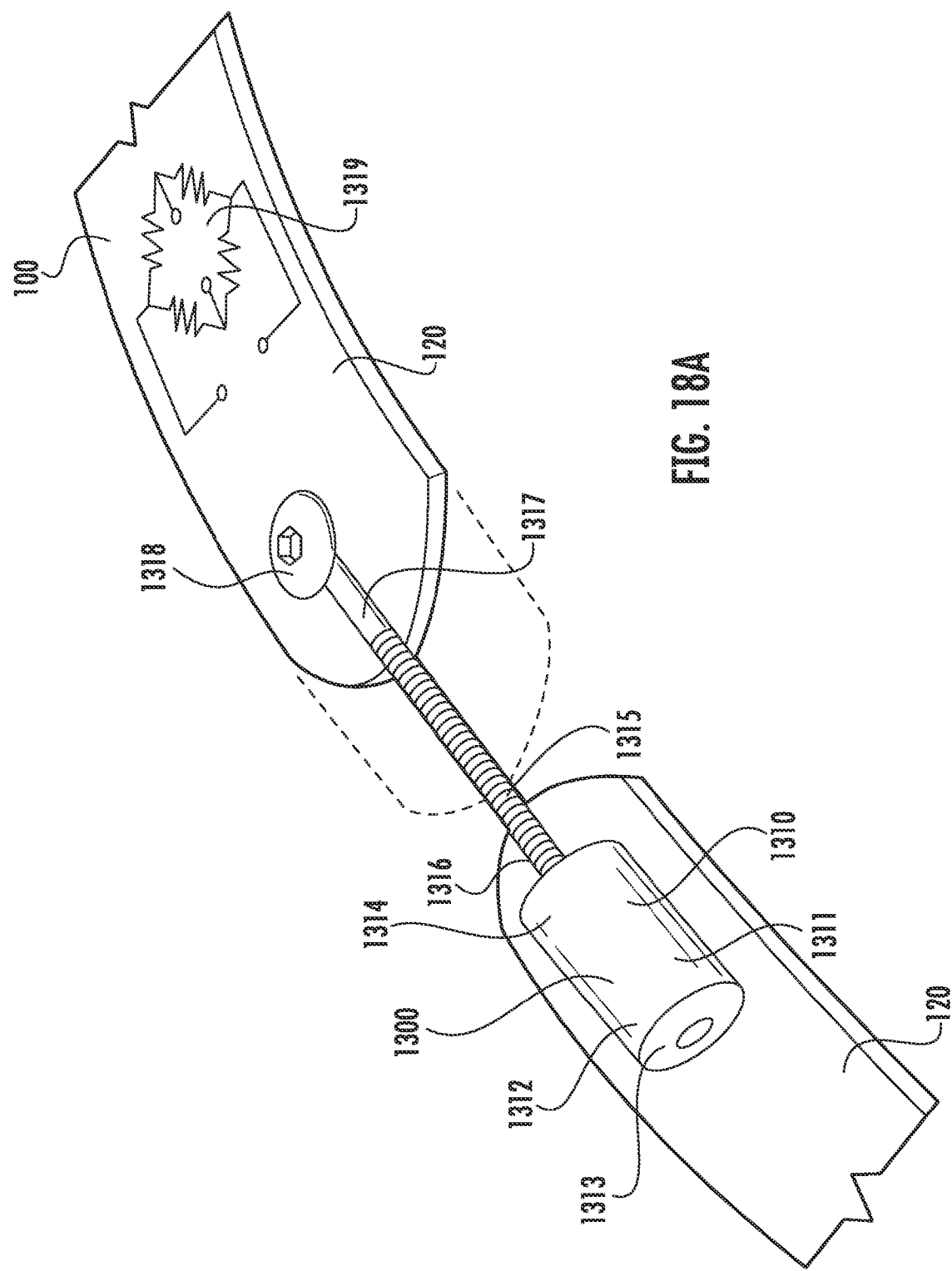
FIG. 18(a) illustrates a tension control device positioned next to a pressure sensor.
Figure 18C:
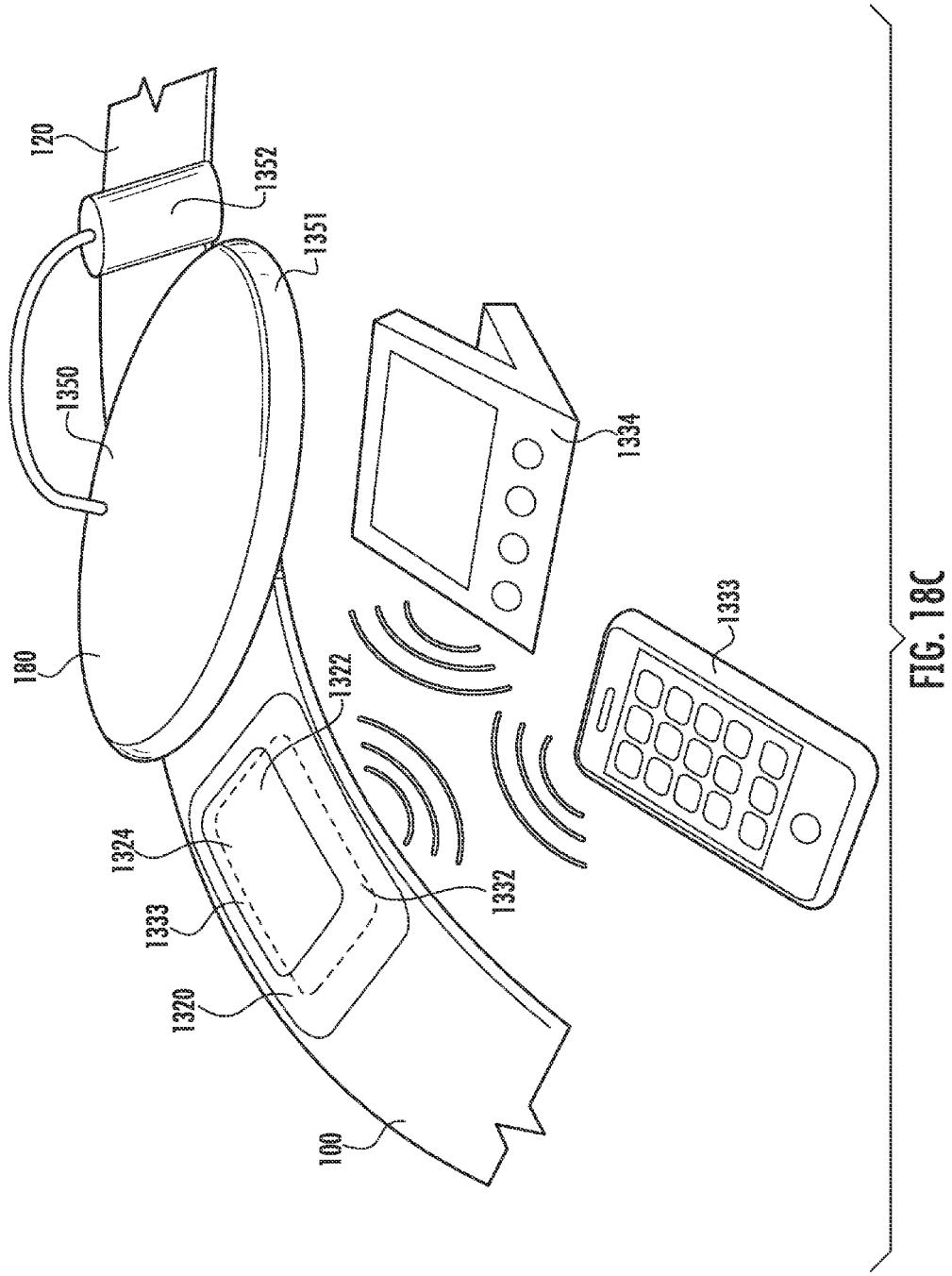
FIG. 18(c) illustrates use of an antenna to uplink information to tablet computers or smart cellular telephones.

As illustrated in FIG. 18A through FIG. 18C, the apparatus 100 further contemplates a controller assembly 1300 (shown specifically in FIG. 18(b)) to both automate and regulate compression onto the user's (U) hips. The controller assembly 1300 may include a variable compression drive 1310, a central controller 1320, a wireless antenna 1332, and one or more pneumatic pads 1350 which include bladders 1351 which can automatically inflate via piston 1352 (illustrated in FIG. 19).

First turning to FIG. 18(a), one component of the controller assembly 1300 is a variable compression drive 1310. Similar in function to the pulley system constricting device 1100 shown the FIG. 13(b), the variable compression drive 1310 constricts and releases each strap 120. Accordingly, such variable compression drive 1310 helps properly position and apply the left pad 180 and corresponding right pad 200 onto the greater trochanters of the female user (U).

The variable compression drive 1310 first includes a rotator drum 1311. The rotator drum 1311 has an outer drum shell 1312, an inner rotator 1313 and a motor 1314. The outer drum 1312 is affixed directly to a first portion of the strap 120. The inner rotator 1313 is threaded and engages a threaded shaft 1315. Put another way, the interior diameter of the inner rotator 1313 is essentially the same as the outer diameter of the threaded shaft 1315. The motor 1314 helps spin the inner rotator 1313 (which is essentially tubular and mirrors the shape of the outer drum shell 1312) which in turn draws the threaded shaft 1315 within the rotator drum 1311 (or alternatively draws out the threaded shaft 1315 to release tension).

The threaded shaft 1315 includes a first end 1316 and corresponding second end 1317. While the inner rotator 1313 connects to the first end 1316 of the threaded shaft 1315, the second end 1317 is affixed to a second portion of the strap 120 through a circular tab 1318. A pressure sensor 1319 is positioned proximate the circular tab 1318 to measure the amount of compression within the strap 120. Optionally, such pressure sensor 1319 may also determine the pressure/force of the strap 120 onto the female user's (U) hips as it can be part of a feedback loop.

This variable compression drive 1310 provides a high degree of precision when adjusting the apparatus 100 onto the user (U). Moreover, it allows customized adjustable compression, as well as usage cycles. For example, the variable compression drive 1310 can allow two minutes of 10 pounds tension, next increasing to 13 pounds of pressure for a five minute period, next dropping to 12 pounds for eight minutes thereafter unloading the compression of the apparatus 100. Moreover, such variable compression drive 1310 can allow vibration to provide therapeutic benefit. While this embodiment includes a rotary motor, such drive could be replaced by a ball screw actuator, worm gear, rack and pinion drive, piezo drive, or any number of rotary or linear actuated devices known to in the art.

Next turning to FIG. 18(b), controller assembly 1300 may also include a central controller 1320 attached to the strap 120. The controller 1320 includes an essentially rectangular housing 1321, a front display 1322 and a plurality of buttons 1329. Positioned within the housing 1321 is a processor 1323, a memory device 1324, and a self-contained power source (which can be a battery). The processor 1323 is capable of receiving machine readable code 1325 from the memory device 1324 in the form of a computer program 1326. Optionally included in the housing 1321 is a speaker 1327 that can provide an audible alarm or provide an audio read out regarding use of the apparatus 100. Such housing 1321 can also include a thermostat 1328 capable of measuring both the outside temperature as well as the temperature of the user's (U) hips. This temperature information can then be posted on the front display 1322 or communicated to an uplink 1330 (described in detail below).

As previously discussed, the memory device 1324 (which can be a flash or hard drive) is capable of storing multiple computer programs 1326. Such programs 1326 can include a countdown timer, a cycle timer (a timer which runs through a sequence of varying compression cycles), monthly timer (timed to denote the user's (U) menstrual cycle and ovulation period) and user password/unlock feature. In addition, the memory device 1324 can include a variety of routines (periods of predetermined constriction and corresponding release of the apparatus 100).

The front display 1321 can have touch screen 1328 capabilities to reduce the need for the operable buttons 1329. Regardless, the front display 1322, touch screen 1328 and operable buttons 1329 allow a user (U) to obtain information about the performance to the apparatus 100 and current settings of the apparatus 100. Moreover, these three devices 1322, 1328 and 1329 allow the user (U) to regulate the compression of the variable compression drive 1310 (shown in FIG. 18(a)) or the pulley system constricting device 1100 shown the FIG. 13(b)).

As further shown in FIG. 18(b), the central controller 1320 is capable of reporting performance data through a variety of uplinks 1330. One form of uplink 1330 contemplated by the invention is a USB port 1331 (which alternatively can be a firewire port, serial port, parallel port or other commercially available port). As illustrated, the USB port 1331 is positioned on the rectangular housing 1321 proximate to the front display 1322. This USB port 1331 allows a computer, laptop, tablet computer 1334, PDA, smart cellular telephone 1333 or similar computing device (illustrated in FIG. 18(c)) to connect to the memory device 1323 positioned within the rectangular housing 1321. This allows the apparatus 100 to report to an outside computing device information such as the total number of times used during a menstrual cycle (i.e., frequency of use), the maximum compression requested by the user (U), temperature readings of the user (U) and a report of the various routines/compression cycles performed.

Alternatively, an antennae 1332 can be employed as the uplink 1330. Such antennae 1332 can communicate with an external computer, laptop, tablet computer 1334, PDA or smart cellular telephone 1333 (illustrated in FIG. 18(c)) through Bluetooth, radio, cellular or wireless transmission. This allows the memory device 1324 to routinely back up and report performance data of the apparatus 100 to another computer device. Moreover, it allows an outside source to interpolate the performance data to determine if there are any anomalies, medical issues, or health risks associated with the user (U) employing the apparatus 100.

Also further contemplated by the apparatus 100 shown in FIG. 18(b), a computer program 1326 stored in the memory device 1324 and used by the processor 1323 can ensure that a user (U) does not select a compression value sufficient to cause injury. More specifically, the central controller 1320 is in direct communication (either via wire or wirelessly via antennae 1332) to the pressure sensor 1319 (shown and illustrated in FIG. 18(a)) positioned on top or within the strap 120. Should such pressure sensor 1319 report to the central controller 1320 a compression value that is greater than a predetermined threshold, then the computer program 1326 will command the compression drive 1310 (or related comparable compression assembly) to reduce the compression to an appropriate level. Alternatively, a similar signal and result can occur if the pressure sensor 1319 reports an elevated compression/constriction within the strap 120.

FIG. 18(c) illustrates the ability of the central computer 1320 to communicate with outside computing devices to maximize the health benefits of the apparatus 100. In one example, the antenna 1332 communicates performance data to a smart cellular telephone 1333 (such as a Blackberry™ or iPhone™). In turn the smart cellular telephone 1333 can interpolate data (through an iPhone application or similar program) received from the memory device 1324. This can generate a series of alarms, such as overuse of the apparatus 100, or too high of compression settings (as reported by the pressure sensor 1319 illustrated in FIG. 18(a)).

Review of performance data for longer periods of time can reveal additional medical issues. For example, an outside tablet computer 1334 communicating via antenna 1332 with the memory device 1324 could look at months of performance information to determine an issue with irregular menstrual cycles. Alternative, such longer periods of information could suggest improper timed use of the apparatus 100 in reference to projected menstrual cycles (i.e., the user (U) is employing the apparatus 100 at the wrong time during each menstrual cycle).

Such performance information stored on the memory device 1324 could then be relayed to the user's (U) healthcare provider, so that her doctor could be put on notice. By providing this performance data (and related alerts) to the healthcare provider, the doctor can give a prognosis or require a visit to address any potential health issues. In addition, such performance data could be reviewed by the healthcare provider's digital medical records to determine any possible health risks—which could then in turn be communicated to front display 1322, tablet computer 1334 and/or smart cellular telephone 1333.

The controller assembly 1300 further contemplates use of an automated pneumatic pad 1350 shown in FIG. 19, which similar to the inner bladder 661 system illustrated in FIG. 14(b). As shown in FIG. 19, each pneumatic pad 1350 includes an inner bladder 1351 surrounded by an exterior sheath 1352. Such exterior sheath 1351 is preferably air tight and/or water tight and is of a sufficient size and dimension to house and maintain the inner bladder 1351.

Positioned proximate the exterior sheath 1351 is a piston 1352. The piston 1352 includes an outer casing which houses the piston head. The piston 1352 is in fluid communication with a conduit 1353 which in turn connects to the inner bladder 1351. Thus, as the piston head moves within the outer casing, a volume of gas and/or liquid is either displaced into (or alternatively out of) the conduit 1353. Such displacement either inflates (or alternatively deflates) the inner bladder 1351. This creates a customized fit of each pad 180/200 onto the user's (U) hips.

The piston 1352 can be either operate manually through a hand pump 1355 (which can communicate with the inner bladder 1351 via a second conduit 1353 to displace gas and/or liquid). Preferably, the piston 1352 communicates directly with the central controller 1320 (shown in FIG. 18(b)) either via wire (i.e., an uplink 1330) or wirelessly via antennae 1332. By running various programs 1326, the central controller 1320 an direct the piston 1352 to properly inflate the inner bladder 1351 of the pneumatic pad 1350 through continuously checking the pressure sensor 1319 (shown and illustrated in FIG. 18(a)) to determine whether the amount of compression has exceeded a predetermined threshold value.

The Heat/Customizable Therapy Pad

FIG. 20 illustrates an alternative embodiment of the left pad 180 of the apparatus 100 capable of providing customizable therapy (including but certainly not limited to heat) to a user (U). As shown, a heat therapy assembly 1400 (which can be used to provide forms of therapy in addition to heat) includes two primary parts: a female holder 1410 and a removable male heat pad 1420. The female holder 1410 is essentially elliptical and includes an outer ring 1411 and a cavity 1412. Dimensions of the outer ring 1411 mirror the shape of the exterior of the cavity 1412. The female holder 1410 is preferably attached directly to the strap 120.

The male heat pad 1420 is likewise elliptical and has a sufficient size and dimension to be received and then locked within the cavity 1412.

The male heat pad 1420 includes an outer sleeve 1421 as well as an inner customizable conductive core 1422. The outer sleeve 1421 could be made of a breathable fabric or have a disposable pad cover, while the conductive core 1422 could be made of a gel or is a liquid contained within bladder. The male heat paid 1420 could be placed in an oven, microwave or similar heating area to be preheated before positioning within the cavity 1412. Accordingly, it is important for the female holder 1410 to allow this heat to pass through to the user (U). The male heat pad 1420 could also be made of a variable density material or a specific geometry to provide a customized shape to conform to the user's (U) unique body type and hips. Such varying density of the male heat pad 1420 can be configured in order to provide additional specific treatment proximate the greater trochanters.

The Travel Pad

The invention further contemplates an embodiment for use during travel. FIG. 21 offers a foldable pad 1500 (which can alternatively be collapsible) as one primary component of the travel apparatus 100. As shown, the foldable pad 1500 includes a first portion 1510 and a corresponding second portion 1520. Both portions 1510 and 1520 mirror each other in terms of size and orientation. Positioned between both portions 1510 and 1520 is a crease 1530. Such crease 1530 can be as simply as a portion of fabric or as complex as a hinge.

Regardless of structure, the crease 1530 allows the foldable pad 1500 to fold to decrease its size and bulk by 50 percent. Having both the left pad 180 and right pad 200 employing such a foldable pad 1500, the apparatus 100 can be stored in a smaller volume for transport and use while traveling. Additionally, the materials used in this embodiment could be chosen so as to not draw additional attention while traveling from other travelers or travel security officers (and devices used by travel authorities at the airports, etc).

Method of Use

In addition to the apparatus 100, the invention also relates to a specific method of relieving the pain and discomfort associated with menstrual cramping. As previously discussed, the method is designed to reduce the stretching of ligaments and tendons surrounding the uterus during menstruation.

The general method of treatment requires use of an apparatus 100 as described above, or any similar mechanism which allows performance of the steps of: first, dimensioning one or more pads 180 and/or 200 proximate to the greater trochanters of the female user (U) and forming each pad to conform to their hips; second, affixing the pad 180 or pads 180/200 to one or more straps 120 having a first end 280 and a corresponding second end 260 at the opposite portion of the strap(s) 120; third, connecting the first end 280 and second end 260 of each strap 120; and fourth, creating a compression sufficient to compress each pad 180 or pads 180/200 onto the user (U). Between 10 to 15 pounds of pressure should be administered during each treatment, which each session lasting between 5 to 10 minutes after the user (U) reports the menstrual pain or discomfort has subsided. However, individual treatment regiments may vary as to both length and pressure.

Apart from the general method described above, the method of treatment may also include the step of filling an inner bladder 661 with sufficient liquid or gas as to conform with the unique shape of the user's (U) hips, if an internal bladder 661 as described in FIG. 14(*b*) is used. If desired, such bladder 661 could be heated to help further treat and alleviate the pain associated with menstrual cramping.

The method could further include the step of shaping each malleable pad 180 or pads 180/200 to conform with the shape of the user's hips. Moreover, the method could additionally include the step of rotating each pad to a position which further conforms with the shape of the user's (U) hips through use of the rotating member described in FIG. 6 and FIG. 7 above.

Post Treatment Undergarment and Additional Steps

Optionally, the invention further contemplates several pre and post treatment steps for both before and after the user has employed the apparatus 100. One post-treatment includes use of a compression undergarment 1500 shown and illustrated in both FIG. 22(*a*) and FIG. 22(*b*). The overall compression undergarment 1500 can take the general form of a traditional commercially available pair of shorts, skirt, pants, or spanx. One of ordinary skill in the art, upon review of both FIGS. 22(*a*) and 22(*b*) as well as the following disclosure, will understand and recognize additional types of garments which can employ the technology to provide relief from menstrual cramping. While the invention contemplates employing the compression undergarment 1500 as a post-treatment device, such compression undergarment 1500 could be used as a stand-alone device as an alternative to the apparatus 100 described above. Alternatively, a pre-treatment undergarment 1500 can be administered for purposes of identifying the proper placement of the pads of the apparatus 100 (described above).

Figure 22A:
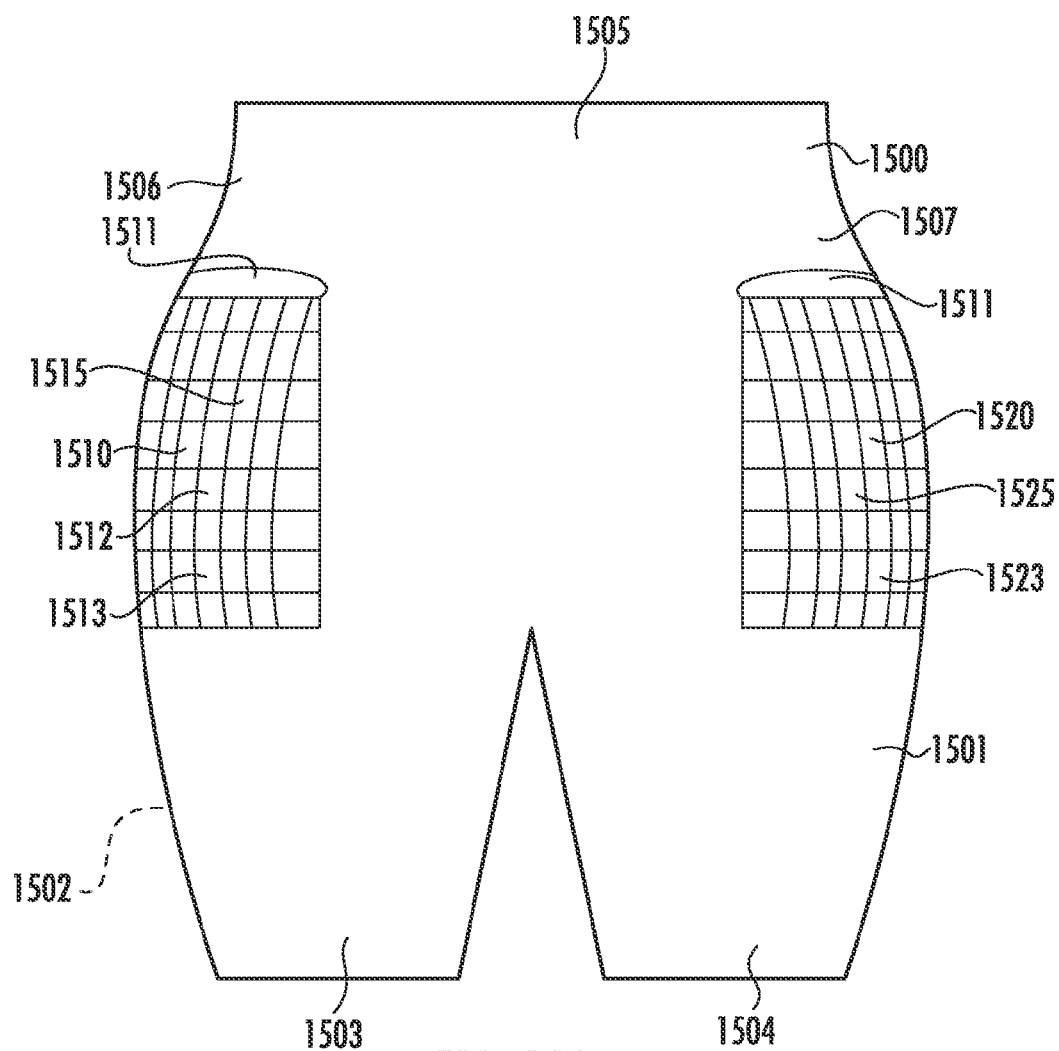
FIG. 22(a) is a front view of a post-treatment compression undergarment which includes a first pad and a corresponding second pad positioned into the undergarment.
Figure 22B:
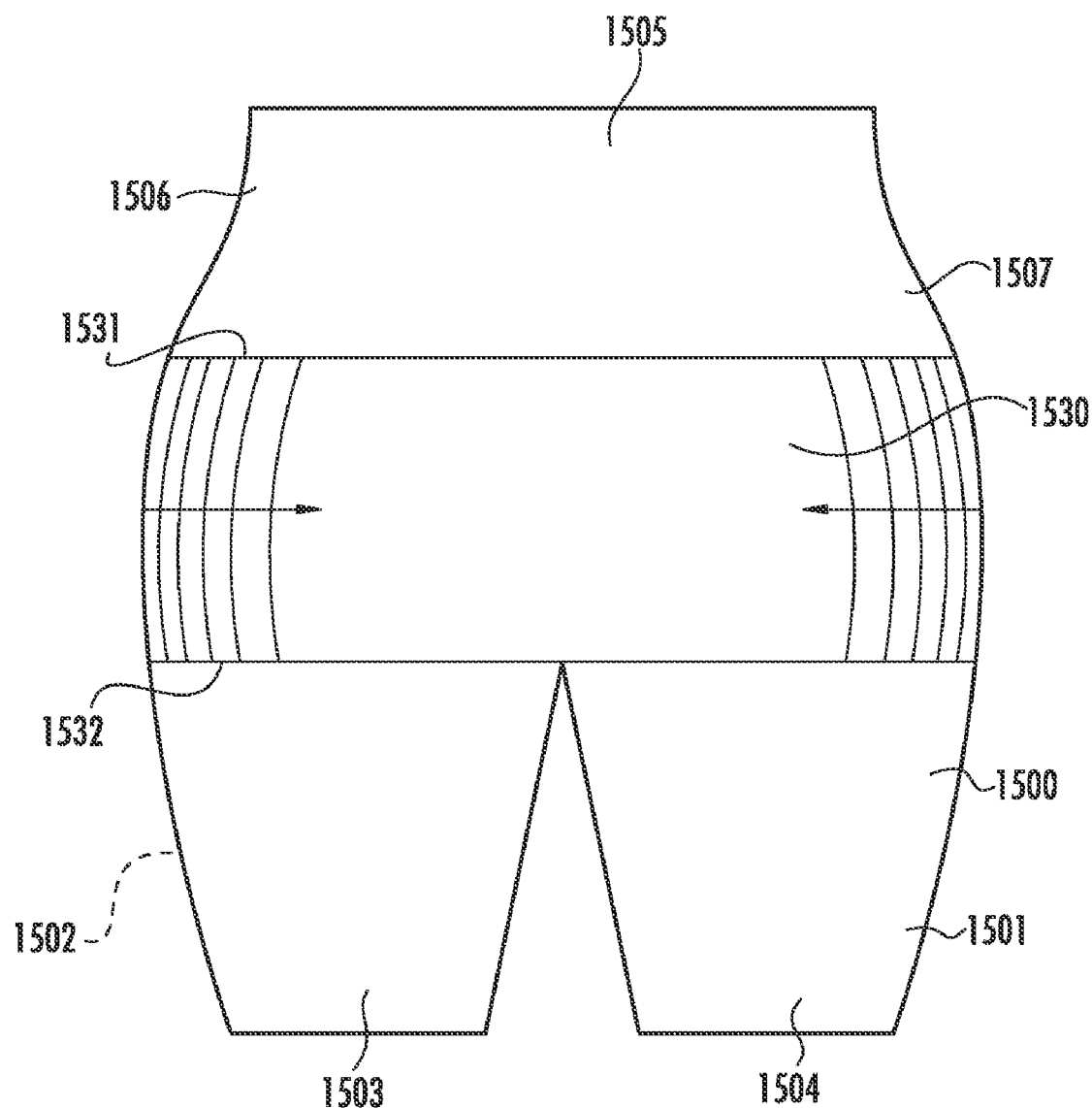
FIG. 22(b) is a front view of a post-treatment compression undergarment which includes additional compression bands.

First turning to FIG. 22(*a*), the overall compression undergarment 1500 includes a front side 1501, corresponding back side 1502, first leg portion 1503 and second leg portion 1504. Positioned above the first leg portion 1503 and second leg portion 1504 is a top portion 1505 (which connects both leg portions 1503 and 1504). This top portion 1505 includes a first side 1506 and corresponding second side 1507 (which mirror each other in dimension and shape).

Positioned proximate the first side 1506 of the top portion 1505 is a first annular sleeve 1510. The first annular sleeve 1510 includes a top opening 1511 and a cavity 1512 which forms a first pocket 1513. Such first annular sleeve 1510 should be positioned along the compression undergarment 1500 so as to be located proximate to one of the user's (U) greater trochanters.

A first pad 1515 is capable of being positioned at the top opening 1511 and then inserted into the cavity 1512. The first annular sleeve 1510 is of a sufficient size and dimension so as to hold and maintain the shape of the first pad 1515. Preferably, the first pad 1515 is sufficiently curved and contoured so as to mirror to shape of the user's (U) hips. Moreover, the first pocket 1513 of the first annular sleeve 1510 is capable of holding and maintaining the curved first pad 1515 while post-treatment is administered.

Correspondingly, a second annular sleeve 1520 is positioned proximate the second side 1507 of the top portion 1505. Mirroring the structure and arrangement of the first annular sleeve 1510, the second annular sleeve 1520 likewise includes a top opening 1511 and a cavity 1512 which forms a second pocket 1523. In addition, this second annular sleeve 1520 should be positioned along the compression undergarment 1500 so as to be located proximate the user's (U) greater trochanters.

A second pad 1525 is capable of being positioned at the top opening 1511 and then inserted into the cavity 1512. The second annular sleeve 1520 is of a sufficient size and dimension so as to hold and maintain the shape of the second pad 1525. Preferably, the second pad 1525 is sufficiently curved and contoured so as to mirror to shape of the user's (U) hips. Moreover, the pocket 1516 of the second annular sleeve 1520 is capable of holding and maintaining the curved second pad 1525 while post-treatment is administered.

Next turning to FIG. 22(*b*), the compression undergarment 1500 can further include one or more elastic compression bands 1530. As shown, the elastic compression band 1530 includes a top edge 1531 and a corresponding bottom edge 1532. Such compression band 1530 is placed over the compression undergarment 1500 such that it covers both the first annular sleeve 1510 and corresponding second annular sleeve 1520 (as shown in FIG. 22(*a*)). Put another way, compression belt 1530 is positioned over both the first pad 1515 and second pad 1525 to engage both pads (1515 and 1525) onto the user's hips proximate the trochanters. By reference, the top edge 1513 of the compression band 1530 should cover the top opening 1511 of both the first pocket 1513 and second pocket 1523 of the compression undergarment 1500.

The invention also contemplates including a plurality of compression bands 1530 for use with the compression undergarment 1500, where each compression band 1530 has a different level of elasticity and compression strength. For example, a user (U) may desire to have lower compression strength and choose a more elastic compression band 1530. Alternatively, a user (U) having a larger degree of menstrual cramping may desire to have a less elastic compression band 1530 to force each of the pads 1515 and 1525 onto the hips of the user (U) proximate the greater trochanters. The invention also contemplates placement of two or more compression bands 1530 on the top portion 1505 of the compression undergarment 1500 to provide relief.

As an alternative, the undergarment 1500 can simply be a device used to locate the greater trochanters of the user (U). As is additionally shown in FIG. 22(*a*), the undergarment 1500 is again in the form of a skirt, shorts, spanks, or brief (or any similar garment known in the art). Such undergarment 1500 includes a first compression aide 1510 (in the form of a graphical representation of a grid), as well as a corresponding second compression aide 1520 (which the same grid demarked). Both compression aides 1510 and 1520 should be positioned proximate the user's (U) greater trochanter to allow a visual point of reference.

In employing such undergarment 1500 (having positioning aides 1510 and 1520), the previous method with first include the pre-administration step of dawning the undergarment 1500 prior to attaching the apparatus 100 (as provided above). This should preferably done through assistance of a medical professional. Once a proper fitting of the apparatus 100 takes place, the undergarment 1500 can be marked along the grid lines of each positioning aide 1510 and 1520 to denote the current location of the left pad 180 and right pad 200. Subsequently, the demarked undergarment 1500 can be used as a pre-treatment step (prior to the method outlined above). Such pre-treatment step would include placing the undergarment on the user (U) and locating the demarked lines. As a second pre-treatment step would include aligning the left pad 180 and right pad 200 of the apparatus 100 to each of the demarked lines within each positioning aide 1510 and 1520. After both pre-treatment steps are performed, the primary treatment method can be performed.

Based upon the structure described above, the post-treatment method first includes the step of placing the first pad 1515 into the top opening 1511 of the first annular sleeve 1510. Next, the second pad 1525 is placed into the second annular sleeve 1520 through the corresponding top opening 1511. As a third step, both pads 1515 and 1525 are positioned within each cavity 1512 of the first pocket 1513 and corresponding second pocket 1523. Such positioning ensures later alignment of each pad 1515 and 1525 proximate to the greater trochanters of the user (U).

With both pads 1515 and 1525 now in place, one or more elastic compression belts 1530 are positioned around the top portion 1505 of the compression undergarment. Such placement can include a single compression belt 1530 or a plurality of compression belts 1530 dependent upon the level of menstrual cramping and individual preferences of the user (U). Care should be given to align the top edge 1531 of the compression bands 1530 to cover both the first annular sleeve 1510 and corresponding second annular sleeve 1520.

Upon this assembly, both the compression undergarment 1500 and compression bands 1530 are placed on the user (U). Some minor adjustments may be necessary for specific placement of both pads 1515 and 1525 to be located proximate the greater trochanters. While the compression undergarment 1500 can be worn for longer periods of time (in comparison to the apparatus 100 shown and illustrated in the Figures above), the compression undergarment 1500 should not be work for more than approximately eight hours at a time.

It is important to note that the compression undergarment 1500 identified in FIG. 22(*b*) need not include pads 1515 and 1525, or any form of sleeve or cavity. Rather, it can simply be a form of undergarment 1500 (identified above as having just positioning aides 1510 and 1520), along with some form of compression band 1530—which can be any form of elastic member. Such simply apparatus can be used for post-treatment and well as the only form of treatment for relieving menstrual cramping.

We claim:

1. An apparatus to reduce the effects of menstrual cramping, the apparatus comprising:
    one or more pads having a heat therapy assembly, wherein the heat therapy assembly includes both a female holder and a removable male heat pad, the female holder having a cavity therein, and wherein the removable male heat pad has sufficient size and dimension to be locked within the cavity of the female holder, each of the one or more pads attached to a strap having a first side, a second side, a first end and a corresponding second end at the opposite portion of the strap;
    a first fastener attached to the first end and a corresponding second fastener attached to the second end of the strap; and
    a compression device located proximate to one pad sufficient to create a compression force through the strap when the first fastener and second fastener connect to each other.

2. The apparatus of claim 1, wherein the female holder includes an outer ring and a cavity sufficient to receive the male heat pad.

3. The apparatus of claim 2, wherein the compression device is a variable compression drive having:
    an outer drum shell attached to the strap;
    an inner rotator having an inner diameter that is treaded, the inner rotator shaped to fit within the outer drum shell;

a motor in communications with the inner rotator;
a threaded shaft having a first end and a second end; the threaded shaft having a sufficient size and dimension so as to engage the inner diameter of the inner rotator; and
a tab sufficient to attach the second end of the threaded shaft with the strap.

4. The apparatus of claim 3, further comprising a controller assembly positioned on the strap, the controller assembly having a central controller attached to the strap in communication with the variable compression drive.

5. The apparatus of claim 4, wherein the central controller has an essentially rectangular housing which includes a front display and a plurality of buttons.

6. The apparatus of claim 5, wherein the rectangular housing includes a processor and memory device which are powered by a self contained power source, the memory device capable of storing computer programs in the form of machine readable code.

7. The apparatus of claim 6, wherein the central controller includes an uplink sufficient to connect the memory device within the rectangular housing to report performance data to an outside computing device.

8. The apparatus of claim 7, wherein the central controller communicates with a pressure sensor attached to the variable compression drive to post the compression force on the front display.

9. The apparatus of claim 2, wherein the male heat pad includes an exterior sleeve filled with a gel or liquid capable of conducting heat.

10. An apparatus to reduce the effects of menstrual cramping, the apparatus comprising:
one or more pads, each pad of the one or more pads attached to a strap having a first side, a second side, a first end and a corresponding second end at the opposite portion of the strap;
a first fastener attached to the first end and a corresponding second fastener attached to the second end of the strap;
a variable compression drive located proximate to at least one of the one or more pads sufficient to create a compression force through the strap when the first fastener and second fastener connect to each other; and
a controller assembly having a central controller in communication with the variable compression drive.

11. The apparatus of claim 10, wherein the central controller has an essentially rectangular housing, the housing including a front display and a plurality of buttons.

12. The apparatus of claim 11, wherein the rectangular housing includes a processor and memory device powered by a self contained power source, the memory device capable of storing computer programs in the form of machine readable code.

13. The apparatus of claim 12, wherein the central controller includes an uplink sufficient to connect the memory device within the rectangular housing to report performance data to an outside computing device.

14. The apparatus of claim 13, wherein the central controller communicates with a pressure sensor attached to the variable compression drive to post the compression force on the front display.

15. The apparatus of claim 14, further comprising a computer program operable for sending an alert to the variable compression drive to reduce the compression force should the pressure sensor determine that such compression is above a threshold value.

16. The apparatus of claim 10, wherein the variable compression drive includes:
an outer drum shell attached to the strap;
an inner rotator having an inner diameter that is treaded, the inner rotator shaped to fit within the outer drum shell;
a motor in communication with the inner rotator;
a threaded shaft having a first end and a second end; the threaded shaft having a sufficient size and dimension so as to engage the inner diameter of the inner rotator; and
a tab sufficient to attach the second end of the threaded shaft with the strap.

17. The apparatus of claim 10, wherein the central controller has a temperature sensor capable of reporting on the front display the user's body temperature.

18. The apparatus of claim 10, wherein the central controller includes a speaker to provide an audio alert to the user.

19. An apparatus to reduce the effects of menstrual cramping, the apparatus comprising:
a strap having a first side, a second side, a first end and a corresponding second end at the opposite portion of the strap;
a pneumatic pad having an inner bladder inflatable via a conduit attached to a piston, each wherein the pneumatic pad is attached to the strap;
a first fastener attached to the first end and a corresponding second fastener attached to the second end of the strap;
a compression device located proximate the pneumatic pad sufficient to create a compression force through the strap when the first fastener and second fastener connect to each other; and
a controller assembly having a central controller attached to the strap in communication with the compression device and the pneumatic pad, the central controller having a housing which includes a front display and a plurality of buttons, wherein the housing includes a processor and memory device powered by a self contained power source, and wherein the memory device is further capable of storing computer programs in the form of machine readable code.

* * * * *